(12) United States Patent
Tuszynski et al.

(10) Patent No.: US 12,187,865 B2
(45) Date of Patent: Jan. 7, 2025

(54) POROUS MATERIAL WITH MICROSCALE FEATURES

(71) Applicants: The Regents of the University of California, Oakland, CA (US); The Regents of the University of Michigan, Ann Arbor, MI (US)

(72) Inventors: Mark H. Tuszynski, La Jolla, CA (US); Jeffrey S. Sakamoto, Ann Arbor, MI (US); Kendell M. Pawelec, Howell, MI (US); Yacov Koffler, San Diego, CA (US); Michael Sailor, La Jolla, CA (US); Jonathan Zuidema, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/126,230

(22) Filed: Mar. 24, 2023

(65) Prior Publication Data

US 2023/0323050 A1  Oct. 12, 2023

Related U.S. Application Data

(63) Continuation of application No. 16/738,872, filed on Jan. 9, 2020, now Pat. No. 11,680,143.
(Continued)

(51) Int. Cl.
*C08J 5/18* (2006.01)
*A61F 2/02* (2006.01)
(Continued)

(52) U.S. Cl.
CPC .................. *C08J 5/18* (2013.01); *A61F 2/02* (2013.01); *A61M 31/002* (2013.01); *C08K 3/36* (2013.01);
(Continued)

(58) Field of Classification Search
CPC combination set(s) only.
See application file for complete search history.

(56) References Cited

U.S. PATENT DOCUMENTS

| 4,669,474 A | * | 6/1987 | Barrows | ............ A61B 17/1128 |
| | | | | 606/152 |
| 5,800,758 A | | 9/1998 | Topolkaraev et al. | |

(Continued)

FOREIGN PATENT DOCUMENTS

| AU | 2020206777 | 11/2023 |
| CA | 3126026 | 7/2020 |

(Continued)

OTHER PUBLICATIONS

"Japanese Application Serial No. 2021-564083, Notification of Reasons for Refusal mailed Dec. 19, 2023", w English Translation, 8 pgs.
(Continued)

*Primary Examiner* — Peter A Salamon
(74) *Attorney, Agent, or Firm* — SCHWEGMAN LUNDBEG & WOESSNER, P.A.

(57) ABSTRACT

Provided herein is technology relating to materials having microscale and/or nanoscale features and particularly, but not exclusively, to porous materials comprising microscale features, methods for producing porous materials comprising microscale features, drug delivery vehicles, and related kits, systems, and uses.

13 Claims, 21 Drawing Sheets

Related U.S. Application Data

(60) Provisional application No. 62/790,178, filed on Jan. 9, 2019.

(51) Int. Cl.
*A61M 31/00* (2006.01)
*C08K 3/36* (2006.01)
*A61F 2/30* (2006.01)
*C08K 3/04* (2006.01)
*C08K 3/32* (2006.01)

(52) U.S. Cl.
CPC . *A61F 2002/30316* (2013.01); *C08J 2367/04* (2013.01); *C08K 3/042* (2017.05); *C08K 2003/325* (2013.01); *C08K 2201/011* (2013.01)

(56) References Cited

U.S. PATENT DOCUMENTS

| | | | | |
|---|---|---|---|---|
| 5,814,405 | A * | 9/1998 | Branca | B01D 71/36 428/311.51 |
| 5,925,053 | A * | 7/1999 | Hadlock | A61L 27/383 606/154 |
| 5,948,020 | A * | 9/1999 | Yoon | A61L 31/06 606/154 |
| 5,993,954 | A * | 11/1999 | Radovanovic | B32B 5/22 428/910 |
| 6,602,593 | B1 * | 8/2003 | Callahan | B29C 55/065 428/315.9 |
| 11,680,143 | B2 | 6/2023 | Tuszynski et al. | |
| 2003/0176876 | A1 * | 9/2003 | Chen | A61L 27/56 606/152 |
| 2007/0196638 | A1 * | 8/2007 | Wei | B29C 48/08 264/41 |
| 2008/0118827 | A1 * | 5/2008 | Call | H01M 50/489 429/129 |
| 2011/0223486 | A1 * | 9/2011 | Zhang | H01M 50/491 521/143 |
| 2011/0300222 | A1 | 12/2011 | Sailor et al. | |
| 2014/0302374 | A1 * | 10/2014 | Wei | B29C 55/005 428/314.2 |
| 2015/0270520 | A1 * | 9/2015 | Stokes | B29C 48/08 429/246 |
| 2016/0013461 | A1 * | 1/2016 | Mizuno | H01M 10/0525 264/41 |
| 2016/0167291 | A1 * | 6/2016 | Zagl | B32B 27/322 428/314.2 |
| 2017/0297292 | A1 | 10/2017 | Maschino et al. | |
| 2018/0185542 | A1 * | 7/2018 | Shen | C08J 5/18 |
| 2018/0243666 | A1 * | 8/2018 | Karabacak | B01J 20/3078 |
| 2018/0280580 | A1 | 10/2018 | Sakamoto et al. | |
| 2020/0354533 | A1 | 11/2020 | Tuszynski et al. | |
| 2021/0236958 | A1 | 8/2021 | Karabacak et al. | |

FOREIGN PATENT DOCUMENTS

| | | |
|---|---|---|
| CN | 1183051 | 5/1998 |
| CN | 114340688 | 12/2023 |
| JP | H11504341 | 4/1999 |
| JP | 2000072910 | 3/2000 |
| JP | 2009202532 | 9/2009 |
| JP | 2013023527 | 2/2013 |
| JP | 2017511403 | 4/2017 |
| JP | 6321914 | 4/2018 |
| JP | 2022517699 | 3/2022 |
| WO | 9634634 | 11/1996 |
| WO | 2010040129 | 4/2010 |
| WO | 2010096733 | 8/2010 |
| WO | 2017031524 | 3/2017 |
| WO | 2020146658 | 7/2020 |

OTHER PUBLICATIONS

"European Application Serial No. 20739136.8, Indication of deficiencies in a request under Rule 22 EPC mailed Jan. 9, 2024", 2 pgs.
"Chinese Application Serial No. 2020800133.55.8, Response Filed Sep. 14, 2023 to Consultation by Telephone in Person mailed Sep. 13, 2023.", W English Claims, 8 pgs.
"International Application Serial No. PCT US2020 012966, Invitation to Pay Additional Fees mailed Mar. 19, 2020", 2 pgs.
"U.S. Appl. No. 16/738,872, Preliminary Amendment Filed May 4, 2020", 8 pgs.
"International Application Serial No. PCT US2020 012966, International Search Report mailed Jul. 1, 2020", 5 pgs.
"International Application Serial No. PCT US2020 012966, Written Opinion mailed Jul. 1, 2020", 8 pgs.
"International Application Serial No. PCT US2020 012966, International Preliminary Report on Patentability mailed Jul. 22, 2021", 11 pgs.
"Chinese Application Serial No. 202080013355.8, Office Action mailed Aug. 25, 2021", with English translation, 2 pages.
"European Application Serial No. 20739136.8, Indication of deficiencies in a request under Rule 22 EPC mailed Dec. 7, 2021", 2 pgs.
"Chinese Application Serial No. 202080013355.8, Notification to Make Rectification mailed Dec. 31, 2021", w English machine translation, 5 pgs.
"U.S. Appl. No. 16/738,872, Restriction Requirement mailed Feb. 8, 2022", 10 pgs.
"European Application Serial No. 20739136.8, Response to Communication pursuant to Rules 161(2) and 162 EPC filed Mar. 8, 2022", 7 pgs.
"U.S. Appl. No. 16/738,872, Response filed Mar. 28, 2022 to Restriction Requirement mailed Feb. 8, 2022", 6 pgs.
"Canadian Application Serial No. 3,126,026, Non Final Office Action mailed Apr. 8, 2022", 4 pgs.
"Australian Application Serial No. 2020206777, First Examination Report mailed Jul. 6, 2022", 5 pgs.
"European Application Serial No. 20739136.8, Communication Pursuant to Rule 22 and Article 113 EPC mailed Jun. 28, 2022", 2 pgs.
"Chinese Application Serial No. 202080013355.8, Response Filed Jul. 27, 2022 to Notification of Paying the Restoration Fee mailed Jun. 8, 2022", 3 pgs.
"Canadian Application Serial No. 3,126,026, Response Filed Aug. 8, 2022 to Non Final Office Action mailed Apr. 8, 2022", 9 pgs.
"Chinese Application Serial No. 202080013355.8, Office Action mailed Sep. 28, 2022", w English translation, 18 pgs.
"U.S. Appl. No. 16/738,872, Non Final Office Action mailed Oct. 5, 2022", 9 pgs.
"European Application Serial No. 20739136.8, Extended European Search Report mailed Sep. 22, 2022,", 7 pgs.
"Canadian Application Serial No. 3,126,026, Office Action mailed Nov. 18, 2022", 3 pgs.
"U.S. Appl. No. 16/738,872, Response filed Jan. 5, 2023 to Non Final Office Action mailed Oct. 5, 2022", 8 pgs.
"U.S. Appl. No. 16/738,872, Notice of Allowance mailed Jan. 27, 2023", 11 pgs.
"U.S. Appl. No. 16/738,872, Corrected Notice of Allowability mailed Feb. 15, 2023", 8 pgs.
"Canadian Application Serial No. 3,126,026, Response Filed Mar. 16, 2023 to Office Action mailed Nov. 18, 2022", 8 pgs.
"Chinese Application Serial No. 202080013355.8, Response Filed Apr. 13, 2023 to Office Action mailed Sep. 28, 2022", With English Claims, 17 pgs.
"European Application Serial No. 20739136.8, Response Filed Apr. 20, 2023 to Extended European Search Report mailed Sep. 22, 2022", 13 pgs.
"Australian Application Serial No. 2020206777, Subsequent Examiners Report mailed Jun. 15, 2023", 3 pgs.
"Australian Application Serial No. 2020206777, Response Filed Jun. 14, 2023 to First Examination Report mailed Jul. 6, 2022", 26 pgs.
"Chinese Application Serial No. 202080013355.8, Office Action mailed Jun. 17, 2023", W English Translation, 9 pgs.

(56) References Cited

OTHER PUBLICATIONS

"Australian Application Serial No. 2020206777, Response Filed Jun. 30, 2023 to Subsequent Examiners Report mailed Jun. 15, 2023", 11 pgs.
Zhang, "Poly(lactide-co-glycolide) Hydroxyapatite Porous Scaffold with Microchannels for Bone Regeneration", Polymers, 8(6), (Jun. 7, 2016), 11 pgs.
"Japanese Application Serial No. 2024-098215, Voluntary Amendment filed Jul. 18, 2024", w/ English claims, 4 pgs.

* cited by examiner

POROUS MATERIAL WITH MICROSCALE FEATURES

CROSS-REFERENCE TO RELATED APPLICATIONS

This application is a continuation of and claims priority to U.S. application Ser. No. 16/738,872, filed Jan. 9, 2020, which claims priority to U.S. Provisional Appl. Ser. No. 62/790,178, filed Jan. 9, 2019, each of which is incorporated by reference as if fully set forth herein.

FIELD

Provided herein is technology relating to materials having microscale and/or nanoscale features and particularly, but not exclusively, to porous materials comprising microscale features, methods for producing porous materials comprising microscale features, drug delivery vehicles, and related kits, systems, and uses.

BACKGROUND

Intrinsically porous materials having microscale features (e.g., in the range of approximately 10 µm to 1 mm) and a high aspect ratio are difficult to manufacture at scaled-up production amounts and/or with high throughput. While methods exist for producing materials having features in the microscale range, these extant technologies have a limited usefulness. For example, conventional machining methods can produce features in a variety of materials and over a range of scales, but machining methods are not applicable to producing three-dimensional high aspect ratios in the microscale range and they do not work well on many polymeric materials. Additionally, extrusion technologies can produce high aspect ratios in a variety of shapes and is applicable to many polymers. However, extrusion cannot produce materials having high percentages of porosity (e.g., greater than approximately 30 vol %) while maintaining microscale features. Furthermore, extrusion technologies are limited in the complexity of shapes that can be produced. Three-dimensional printing technologies are increasingly transitioning to microscale production, but UV-curing technologies, by far the most common type of three-dimensional printing technologies, are hindered by the "bleed" of features, especially at small scales. Accordingly, three-dimensional printing technologies are limited both in the feature size achievable and it the aspect ratio of the printed material. Dip-coating methods can be used to produce microscale features from porous polymers at high aspect ratios, but are limited to producing simple shapes in batch processes and are not high-throughput. Thus, new methods for producing porous materials having microscale features are needed.

SUMMARY

Accordingly, provided herein is technology relating to materials having microscale and/or nanoscale features and particularly, but not exclusively, to porous materials comprising microscale and/or nanoscale features, methods for producing porous materials comprising microscale and/or nanoscale features, and related kits, systems, and uses. In some embodiments, the technology comprises embossing a polymer composition to produce a porous material comprising microscale and/or nanoscale features. In some embodiments, the technology comprises embossing thin films (e.g., thin polymer films). In some embodiments, materials produced according to the technology provided herein comprise homogeneous features and/or wall thicknesses of less than 100 µm (e.g., less than approximately 100, 95, 90, 85, 80, 75, 70, 65, 60, 55, 50, 45, 40, 35, 30, 25, 20, 15, or 10 µm). In some embodiments, the technology produces a material comprising a first composition and a second composition. In some embodiments, the second composition is a porogen. In some embodiments, embodiments of the embossing technology described herein produce a material comprising a second composition that is a functional composition and/or a layer added to another, first composition. Conversely, in some embodiments, the second composition is subsequently removed from the first composition after forming the material, thus producing a void space in the first composition (e.g., in the material comprising the first composition). Accordingly, in some embodiments, materials produced according to the technologies described herein have a large open lumen volume, have a high surface-to-volume ratio, and/or have a high permeability to fluid (e.g., gas and/or liquid) flow. In some embodiments, materials produced according to the technology comprise porous scaffold walls and, accordingly, the materials comprise aligned microchannel features having a high aspect ratio and good flexibility.

The technology provides advantages relative to extant technologies (e.g., extrusion and dip-coating). For example, in some embodiments, materials produced according to the technology provided herein comprise reproducible and homogeneous microscale features and/or channels (e.g., features having a size in the range of approximately 1 µm to 1 mm (e.g., approximately 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm)). In some embodiments, materials produced according to the technology provided herein comprise pores, e.g., having a hierarchical porosity. In some embodiments, materials produced according to the technology provided herein comprise a high percentage of interconnecting porosity (e.g., 0 to 80 vol % (e.g., 0, 5, 10, 15, 20, 25, 30, 35, 40, 45, 50, 55, 60, 65, 70, 75, 80 vol %)) in microchannel walls.

In some embodiments, materials produced according to the technology provided herein comprise pores that are in a range of approximately 100 nm to 10 µm (e.g., approximately 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nm).

In some embodiments, the technology comprises use of roll-to-roll processing technology (e.g., high-throughput roll-to-roll processing technology).

In some embodiments, materials produced according to the technology provided herein comprise a plurality of compositions. For example, in some embodiments, materials produced according to the technology provided herein comprise a first composition and a second composition. In some embodiments, a first composition comprises (e.g., encloses) a second composition that is a porogen. In some embodiments, a first composition comprises (e.g., encloses) a second composition and the second composition is subsequently removed to provide a void space in the first composition (e.g., to provide a material comprising the first composition and void space). The technology is not limited in the compositions used to produce the materials. For example, in some embodiments, the technology comprises use of a polymer composition (e.g., polycaprolactone (PCL), poly(lactic-co-glycolic acid) (PLGA), etc.).

In some embodiments, materials produced according to the technology provided herein have features in the range of approximately 1 μm to 1 mm (e.g., approximately 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm) and have a high open lumen volume (e.g., approximately 30% to 90% (e.g., 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90%).

In some embodiments, materials produced according to the technology provided herein have features in the range of approximately 1 μm to 1 mm (e.g., approximately 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm) and are produced by embossing a thin polymer film (e.g., having a thickness of less than 100 μm (e.g., less than 10, 15, 20, 25, 30, 35, 40, 45, 50, 55, 60, 65, 70, 75, 80, 85, 90, 95, 100, 105, 110, 115, 120, 125, 130, 135, 140, 145, or 150 μm).

In some embodiments, materials produced according to the technology provided herein comprises a first composition having features in the range of approximately 1 μm to 1 mm (e.g., approximately 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm) and comprises a second composition that is a drug and/or therapeutic.

Embodiments provide that producing features in the material and functionalizing the material are decoupled. For example, in some embodiments, the materials comprise a composition (e.g., a polymer film) that is embossed and that comprises a chemical modification on one side.

The technology finds use in a number of fields. For example, embodiments of the materials provided herein find use in tissue engineering, e.g., tissue engineered scaffold technology. In particular embodiments, the technology finds use in nerve repair. In some embodiments, the technology finds use in other engineering applications using materials having similar structures, permeabilities, and fluid (e.g., gas and/or liquid) flow, e.g., catalysts, fuel cells, etc. In some embodiments, the technology is appropriate for scalable batch sizes. In some embodiments, the technology finds use in producing a medical device (e.g., a tissue scaffold) that is introduced into a patient. In some embodiments, the technology provides matching the size (e.g., length, width, diameter, etc.) of a medical device to fit a particular patient.

Accordingly, in some embodiments, provided herein are embodiments of a porous film material comprising microscale features and a porosity of 60% vol or more. In some embodiments, the microscale features are channels having an aspect ratio of 100 or more. In some embodiments, the porous film material comprises a polymer. In some embodiments, the porous film material comprises a biocompatible polymer. In some embodiments, the porous film material comprises a polyester. In some embodiments, the porous film material comprises a polycaprolactone and/or a poly(lactide co-glycolide). In some embodiments, the porous film material comprises two polymer layers surrounding said microscale features. In some embodiments, the porous film material further comprises a filler material. In some embodiments, the filler material comprises an inorganic material. In some embodiments, the filler material comprises a fiber, a particle, or a nanoparticle. In some embodiments, the filler material comprises a metal, a salt, a calcium phosphate, an oxide, a ceramic, and/or a graphite. In some embodiments, the porous film material comprises a porogen. In some embodiments, the porous film material has a thickness of 50-200 μm. In some embodiments, the microscale features of the porous film material have a dimension of from 1 to 1000 μm.

Further embodiments provide a method for producing a porous film material comprising microscale features and a porosity of 60% vol or more. For example, in some embodiments, methods comprise providing a polymer film; and embossing said polymer film to produce said porous film material comprising microscale features. In some embodiments, the polymer film comprises a porosity of 60% vol or more. In some embodiments, the embossing comprises pressing said polymer film against an embossing block comprising microscale features. In some embodiments, the embossing block is heated to 20° C. or more. In some embodiments, the pressing comprises applying a force of at least 0.1 metric tons. In some embodiments, the pressing comprises using a hydraulic press. In some embodiments, providing the polymer film comprises casting a composition comprising a polymer and a porogen. In some embodiments, providing said polymer film comprises washing a film comprising a polymer and a porogen to minimize and/or eliminate the porogen. In some embodiments, the methods further comprise washing said porous film material comprising microscale features and a porosity of 60% vol or more to minimize and/or eliminate the porogen. In some embodiments, methods further comprise contacting said polymer film with a spacer. In some embodiments, embossing comprises pressing said polymer film against a spacer to produce said microscale features in said polymer film. In some embodiments, the polymer film comprises a biocompatible polymer. In some embodiments, the polymer film comprises a polyester. In some embodiments, the polymer film comprises a polycaprolactone and/or a poly(lactide co-glycolide). In some embodiments, methods further comprise reacting a surface of said polymer film with a reagent.

In some embodiments, methods for producing a porous film material comprising microscale features and a porosity of 60% vol or more comprise providing a first polymer film and providing a second polymer film; placing a spacer between said first polymer film and said second polymer film; and embossing said first polymer film and said second polymer film to produce said a porous film material comprising microscale features and a porosity of 60% vol or more. In some embodiments, methods further comprise removing the spacer from said porous film material to leave a void space. In some embodiments, the first polymer film and/or said second polymer film comprises a polymer and a porogen. In some embodiments, providing the first polymer film comprises washing the first polymer film to minimize and/or eliminate a porogen and/or providing the second polymer film comprises washing the second polymer film to minimize and/or eliminate a porogen. In some embodiments, methods further comprise washing the porous film material comprising microscale features and a porosity of 60% vol or more to minimize and/or eliminate a porogen. In some embodiments, the first polymer film has a porosity of 60% vol or more and/or the second polymer film has a porosity of 60% vol or more.

In some embodiments, the technology provides a porous film material comprising microscale features and a porosity of 60% vol or more produced by a method as described herein. For example, in some embodiments, the technology provides a porous film material comprising microscale features and a porosity of 60% vol or more produced by a method comprising the steps of providing a polymer film; and embossing said polymer film to produce said porous film material comprising microscale features. In some embodiments, the technology provides a porous film material comprising microscale features and a porosity of 60% vol or more produced by a method comprising the steps of providing a first polymer film and providing a second polymer film; placing a spacer between said first polymer film and said second polymer film; and embossing said first polymer film and said second polymer film to produce said a porous film material comprising microscale features and a porosity of 60% vol or more.

In some embodiments, the technology provides a device comprising a rolled porous film material comprising microscale features and a porosity of 60% vol or more. In some embodiments, the device further comprises a sheath around the rolled porous film material. In some embodiments, the device comprises a biocompatible polymer. In some embodiments, the device further comprises a cell or tissue. In some embodiments, the device further comprises a nerve tissue, e.g., in some embodiments the device is secured to nerve tissue.

In some embodiments, the device comprises a catalyst material.

The technology finds use in a variety of fields. For example, in some embodiments, the technology relates to use of a porous film material comprising microscale features and a porosity of 60% vol or more as a tissue scaffold. In some embodiments, the technology relates to use of a porous film material comprising microscale features and a porosity of 60% vol or more as a catalyst. In some embodiments, the technology relates to use of a porous film material comprising microscale features and a porosity of 60% vol or more to produce a biomedical device to support tissue growth. In some embodiments, the technology relates to use of a porous film material comprising microscale features and a porosity of 60% vol or more to treat a subject in need of tissue repair or growth.

In some embodiments, the technology provides a system for producing a porous film material comprising microscale features and a porosity of 60% vol or more. For example, in some embodiments, a system comprises a polymer film; and an embossing block comprising microscale features. In some embodiments, systems further comprise one or more spacers. In some embodiments, systems further comprise a porogen. In some embodiments, the polymer comprises a water-soluble salt porogen. In some embodiments, the polymer comprises a filler material. In some embodiments, systems further comprise a sheath. In some embodiments, the polymer film has a porosity of 60% vol or more. And, in some embodiments, systems further comprise a hydraulic press.

In some system embodiments for producing a porous film material comprising microscale features and a porosity of 60% vol or more, systems comprise a composition comprising a polymer; and an embossing block comprising microscale features. In some embodiments, systems further comprise one or more spacers. In some embodiments, systems further comprise a porogen. In some embodiments, systems further comprise a porogen comprising a water-soluble salt. In some embodiments, systems further comprise a filler material.

Furthermore, some embodiments of the technology relate to devices and materials comprising therapeutic-loaded nanoparticles, e.g., for use as an implantable device for delivery of a therapeutic. In some embodiments, the technology provides an implantable device providing spatial and temporal control of the delivery of a therapeutic. Accordingly, in some embodiments the technology provides a porous film material as described herein further comprising a therapeutic-loaded nanoparticle (e.g., a therapeutic-loaded porous silicon nanoparticle). In some embodiments, the porous film material comprises between 0.01 and 99% wt (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% wt) therapeutic-loaded nanoparticles, between 0.01 and 50% wt (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% wt) therapeutic-loaded nanoparticles, or between 1 and 30% wt (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0% wt) therapeutic-loaded nanoparticles.

In related embodiments, methods comprise providing a polymer film comprising therapeutic-loaded nanoparticles; and embossing said polymer film to produce said porous film material comprising microscale features. In some embodiments, methods comprise loading nanoparticles with a therapeutic. In some embodiments, the technology provides a method for producing a porous film material comprising microscale features and a porosity of 60% vol or more, said method comprising providing a first polymer film and providing a second polymer film; placing a spacer between said first polymer film and said second polymer film; and embossing said first polymer film and said second polymer film to produce said a porous film material comprising microscale features and a porosity of 60% vol or more, wherein the first and/or the second polymer film comprises therapeutic-loaded nanoparticles. In some embodiments, the method comprises loading nanoparticles with a therapeutic Related embodiments provide a device comprising a rolled porous film material comprising microscale features and a porosity of 60% vol or more, wherein the porous film material comprising therapeutic-loaded nanoparticles. In some embodiments, the device comprises a porous film material comprising a first region comprising a first therapeutic and a second region comprising a second therapeutic. In some embodiments, the device comprises a porous film material comprising a first region comprising a first concentration of a therapeutic and a second region comprising a second concentration of said therapeutic. In some embodiments, the technology relates to use of a device as an implantable therapeutic-delivery device.

In some embodiments, the technology provides a system for producing a porous film material comprising microscale features and a porosity of 60% vol or more. In some embodiments, the system comprises a polymer film; and an embossing block comprising microscale features, wherein the polymer film comprises therapeutic-loaded nanoparticles. In some embodiments, the technology provides system for producing a porous film material comprising microscale features and a porosity of 60% vol or more. In some embodiments, the system comprises a composition comprising a polymer; and an embossing block comprising microscale features, wherein the composition comprises therapeutic-loaded nanoparticles.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 7A shows measurements of compression and FIG. 7B shows measurements of 3-point bending. The data indicate that the hydrated devices produced by the embossing methods described herein were easily compressed (FIG. 7A) and bent (FIG. 7B). The microchannel devices made according to embodiments of the embossing methods had equal or greater compliance (e.g., a measure of how easily the material can be compressed) than dip-coated devices. A large range of properties was observed, depending on the material used. The devices tested were 1.5 mm in diameter and 15 mm long. The inset photographs show the tests being performed.

Figure 1:
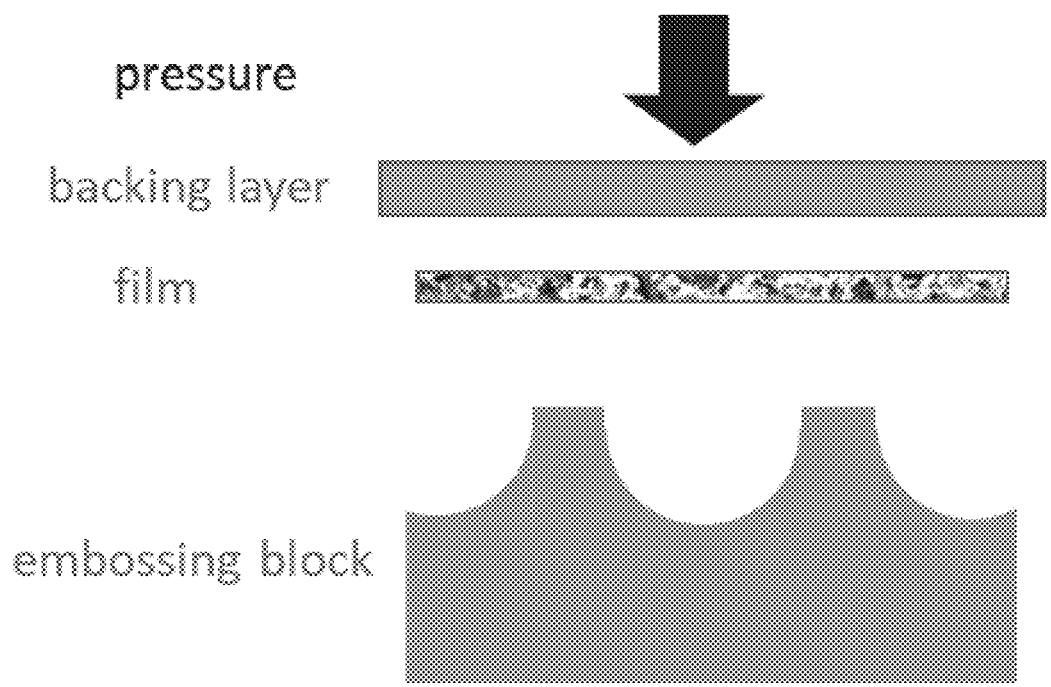
FIG. 1 is a schematic drawing showing components related to embodiments of the technology for producing an embossed polymer film. The drawing shows a film pressed to an embossing block comprising linear features. A backing layer is placed between the film and the component applying pressure to the film.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION

Provided herein is technology relating to materials having microscale and/or nanoscale features and particularly, but not exclusively, to porous materials comprising microscale features, methods for producing porous materials comprising microscale features, and related kits, systems, and uses. In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

When a component, element, composition, material, or layer is referred to as being "on", "engaged to", "connected to", or "coupled to" another component, element, composition, material, or layer, it may be directly on, engaged, connected, or coupled to the other component, element, composition, material, or layer, or intervening elements or layers may be present. In contrast, when a component, element, composition, material, or layer is referred to as being "directly on", "directly engaged to", "directly connected to", or "directly coupled to" another component, element, composition, material, or layer, there may be no intervening component, element, composition, material, or layer present. Other words used to describe the relationship between components, elements, compositions, materials, or layers should be interpreted in a like fashion (e.g., "between" versus "directly between", "adjacent" versus "directly adjacent", etc.).

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

Spatially or temporally relative terms, such as "before", "after", "inner", "outer", "beneath", "below", "lower", "above", "upper", and the like, may be used herein for ease of description to describe one element or feature's relationship to another element(s) or feature(s), e.g., as illustrated in the figures. Spatially or temporally relative terms may be intended to encompass different orientations of the device or system in use or operation in addition to the orientation depicted in the figures.

As used herein, the term "channel" refers to a structure comprising a longitudinal axis and having an open lumen. In some embodiments, channels have a longitudinal axis that is longer than the other dimensions (e.g., diameter or width) of the channel. In some embodiments, a channel has an aspect ratio that is greater than 100 (e.g., greater than 100, 150, 200, 250, 300, 350, 400, 450, 500, 550, 600, 650, 700, 750, 800, 850, 900, 950, or 1000); greater than 1000 (e.g., greater than 1000; 1500; 2000; 2500; 3000; 3500; 4000; 4500; 5000; 5500; 6000; 6500; 7000; 7500; 8000; 8500; 9000; 9500; or 10,000); or greater than 10,000 or more (e.g., greater than 10,000; 15,000; 20,000; 25,000; 30,000; 35,000; 40,000; 45,000; 50,000; 55,000; 60,000; 65,000; 70,000; 75,000; 80,000; 85,000; 90,000; 95,000; or 100,000).

As used herein, the term "aspect ratio" refers to a length of the longest axis of a structure or feature (e.g., a channel) divided by diameter of the structure or feature (e.g., a channel). In some embodiments, the aspect ratio of a structure or feature (e.g., a channel) is greater than 100 (e.g., greater than 100, 150, 200, 250, 300, 350, 400, 450, 500, 550, 600, 650, 700, 750, 800, 850, 900, 950, or 1000). In some embodiments, the aspect ratio of a structure or feature (e.g., a channel) is greater than 1000 (e.g., greater than 1000; 1500; 2000; 2500; 3000; 3500; 4000; 4500; 5000; 5500; 6000; 6500; 7000; 7500; 8000; 8500; 9000; 9500; or 10,000). In some embodiments, the aspect ratio of a structure or feature (e.g., a channel) is greater than 10,000 or more (e.g., greater than 10,000; 15,000; 20,000; 25,000; 30,000; 35,000; 40,000; 45,000; 50,000; 55,000; 60,000; 65,000; 70,000; 75,000; 80,000; 85,000; 90,000; 95,000; or 100,000).

As used herein, the term "micro" (e.g., as used in "microsized", "microscale", "micro-feature", or "micrometer-sized" refers to a size that is less than approximately 1000 micrometers (μm) (e.g., less than approximately 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm).

As used herein, the term "nano" (e.g., as used in "nano-sized", "nanoscale", or "nanometer-sized" refers to a size that is less than approximately 1000 nanometers (nm) (e.g., less than approximately 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nm).

As used herein, the term "microchannel" refers to a channel having at least one spatial dimension that is less than approximately 1000 μm.

As used herein, the term "biocompatible" refers to a material, composition, or combination of materials or compositions that can contact cells or tissues (e.g., in vitro or in vivo) or that can be used with an animal (e.g., mammal) and has acceptable toxicological properties for contact and/or beneficial use with such cells, tissue, and/or animals. For example, in some embodiments a biocompatible material is a material that is suitable for implantation into a subject without adverse consequences and/or without substantial toxicity or acute or chronic inflammatory response and/or without acute rejection of the material by the immune system (e.g., via a T-cell response in the subject). It will be recognized that "biocompatibility" is a relative term and some degree of inflammatory and/or immune response is to be expected even for materials that are highly compatible with living tissue. However, non-biocompatible materials are typically those materials that are highly toxic, inflammatory, and/or are acutely rejected by the immune system, e.g., a non-biocompatible material implanted into a subject may provoke an immune response in the subject that is severe enough such that the rejection of the material by the immune system cannot be adequately controlled, in some cases even with the use of immunosuppressant drugs, and often can be of a degree such that the material must be removed from the subject. In certain aspects, biocompatible materials are those that are approved for use in humans by an appropriate regulatory agency, e.g., the Federal Drug Administration (FDA) in the United States; the European Commission (EC)/European Medicines Agency (EMEA) in Europe; or Health Products and Food Branch (HPFB) in Canada. In some embodiments, a biocompatible material is biodegradable. For example, in some embodiments, a biocompatible material is a biocompatible polymer. As used herein, the term "biocompatible polymer" refers to any artificial or natural biodegradable or non-degradable polymer such as, for example, but not limited to; collagen, gelatin, chitosan, carrageenan, alginate, hyaluronic acid, dextran, poly(lactic acid), poly(glycolic acid) (PGA), poly(lactic-co-glycolic acid) (PLGA), poly(ε-caprolactone), poly(anhydrides), polyorthoesters, polyvinyl alcohol, poly(ethylene glycol), polyurethane, poly(acrylic acid), poly(N-isopropyl acrylamide), poly(ethylene oxide)-poly(propylene oxide)-poly(ethylene oxide) copolymer (PLURONIC), a copolymer thereof, or a mixture thereof.

As used herein, the term "porosity" refers to a measurement of the void space(s) in a material and is expressed as a ratio of the volume of the total void space(s) over the total volume of the material (e.g., sum of total void and total non-void spaces). Porosity is expressed as a fraction between 0 and 1 or as an equivalent percentage expressed as "vol %". In some embodiments, non-void volume is occupied by a solid material and the void volume is occupied by a fluid (e.g., gas and/or liquid). For example, as used herein, the term "open lumen volume" refers to the volume within a material (e.g., a scaffold) that is not occupied by scaffold walls.

As used herein, the term "porous tissue scaffold" and "porous scaffold" are used interchangeably and refer to a three-dimensional molecular matrix of biocompatible polymers for attachment and growth of tissue cells.

As used herein, the term "in-vitro culturing system" refers to a system configured to grow cells, tissues, organs, or parts of organs ex-vivo.

As used herein, the term "biocompatible article" refers to a material used for the treatment of a medical condition or for a cosmetic correction where the material is placed on or in the body of a human or an animal and that does not evoke an adverse immunologic response. In some embodiments, a biocompatible article comprises materials that degrade and/or are absorbed by the body over time. In some embodiments, a biocompatible material is a bandage, powder, sponge, hemostat, suture, implant, injectable particle, microsphere, microcarrier, gel, or putty.

As used herein, the terms "pluripotent", "pluripotency", "pluripotent cells", and equivalent expressions refer to cells that are capable of both proliferation and self-renewal in cell culture and differentiation towards a variety of cell populations that include those that exhibit multipotent properties. For example, pluripotent embryonic stem (ES) cells can give rise to each of the three embryonic cell lineages. Pluripotency can be demonstrated by providing evidence of stable developmental potential, to form derivatives of all three embryonic germ layers from the progeny of a single cell, and to generate a teratoma after injection into an immunosuppressed mouse. Other indications of pluripotency include expression of genes known to be expressed in pluripotent cells and having a characteristic morphology. The technology is not limited in the use of any particular pluripotent cells and includes pluripotent cells obtained using any method known to those skilled in the art. For example, in some embodiments, "pluripotent cells" include but are not limited to stem cells, induced pluripotent stem cells (iPS cell) (e.g., a human induced pluripotent stem cell (hiPSC), a human embryonic stem cell (hESC), parthenogenic cells, and the like.

As used herein, the term "totipotent" refers to the ability of a cell to develop into all types of cells, including extraembryonic tissues (e.g., placenta) and to give rise to an entire organism (e.g., a mouse or human).

As used herein, a "calender" is an apparatus used to smooth, coat, or thin a material, e.g., by passing the material between calender rollers at high temperatures and pressures.

As used herein, the term "therapeutic" or "therapeutic agent" refers to a compound that, upon administration to a mammal in a therapeutically effective amount, provides a therapeutic benefit to the mammal A therapeutic agent may be referred to herein as a drug. Those skilled in the art will appreciate that the term "therapeutic agent" is not limited to drugs that have received regulatory approval. A therapeutic agent can be a peptide, protein, an antibody, an antibody fragment, or a small molecule (e.g., drug).

Embodiments of the technology provide a material that finds use in tissue repair (e.g., nerve repair). In some embodiments, the material provides support for tissue repair and a high open lumen (e.g., the volume available for tissue (e.g., nerves) to regenerate). In some embodiments, a device comprising the material described herein is placed in a subject at a site of injury to provide tissue regeneration. Accordingly, in some embodiments, the device comprising the material described herein is sufficiently flexible to allow a device comprising the material to be placed at a site of injury without kinking when a subject moves.

In some embodiments, the materials provided herein comprise a synthetic polymer that retains its shape without swelling (e.g., as observed with natural polymers or hydrogels) that reduces the open lumen volume over time (see, e.g., Pawelec et al. (2018) "Microstructure and in vivo characterization of multi-channel nerve guidance scaffolds" Biomedical Materials 13: p. 044104; Shahriari et al. (2017) "Hierarchically ordered porous and high-volume polycaprolactone microchannel scaffolds enhanced axon growth in transected spinal cords" Tissue Engineering Part A 23(9-10): 415-25, incorporated herein by reference). In some embodiments, synthetic polymers are stiffer than hydrogels (and, in some embodiments, native nerve tissue) and have a high strength and stiffness that reduces wall thickness and thus provides a higher open lumen volume (see, e.g., Chen et al. (2011) "Comparison of polymer scaffolds in rat spinal cord: A step toward quantitative assessment of combinatorial approaches to spinal cord repair" Biomaterials 32: 8077-86, incorporated herein by reference). The technology is not limited in the polymer used to produce the materials described herein. Embodiments of the technology comprise a wide range of polymers providing appropriate mechanical and degradation behaviors. In some embodiments, the technology comprises use of an FDA-approved polymer (e.g., that finds use in medical implants). In some particular embodiments the technology provides a material or device comprising a poly(lactide co-glycolide) (PLGA) and/or a poly(caprolactone) (PCL). The chemistries and glass transition temperatures of these two polymers provide particular mechanical properties that are advantageous for embodiments of the materials and devices described herein. (Chen et al. (2011) "Comparison of polymer scaffolds in rat spinal cord: A step toward quantitative assessment of combinatorial approaches to spinal cord repair" Biomaterials 32: 8077-86, incorporated herein by reference). Furthermore, the technology is not limited in the degradation rate (e.g., in vivo) of materials and devices described herein. For example, embodiments provide a material comprising PLGA (e.g., that degrade over a range from weeks to months, depending on the ratio of lactide to glycolide) and some embodiments provide a material comprising PCL (that is resistant to degradation (e.g., remaining in the body for 24 to 36 months)). See, e.g., de Ruiter et al. (2008) "Methods for in vitro characterization of multichannel nerve tubes" Journal of Biomedical Materials Research Part A 84A: 643-51; Woodruff and Hutmacher (2010) "The return of a forgotten polymer-polycaprolactone in the 21st century" Progress in Polymer Science 35: 1217-56, incorporated herein by reference).

Embodiments of the technology provide a device, e.g., a multichannel scaffold. In some embodiments, the device comprises linear microchannels within a larger conduit See, e.g., Yao et al. (2010) "Controlling dispersion of axonal regeneration using a multichannel collagen nerve conduit" Biomaterials 31: 5789-97; Pawelec et al (2018) "Microstructure and in vivo characterization of multi-channel nerve guidance scaffolds" Biomedical Materials 13: 044104; Shahriari, (2017) "Peripheral nerve growth within a hydrogel microchannel scaffold supported by a kink-resistant conduit" Journal of Biomedical Materials Research Part A 105(12): 3392-99; Wang et al. (2017) "Design and optimization of a biodegradable porous zein conduit using microtubes as a guide for rat sciatic nerve defect repair" Biomaterials 131: 145-59, incorporated herein by reference). In some embodiments, the linear microchannels physically guide recapitulation (e.g., in some embodiments, regeneration mimics fascicle architecture in native nerve tracts) and reduces mis-alignment and increasing functional recovery. Further, in some embodiments, the technology provides materials and devices having a monodisperse microchannel diameter, which finds use in producing closely packed materials and devices and, consequently, provides high open lumen volumes.

In some embodiments, the technology provides a multichannel scaffold comprising two components, e.g., a multichannel array and a conduit. In some embodiments, the conduit provides for anastomosis (e.g., between nerve stumps and microchannels), e.g., when placed in a tissue or patient. Accordingly, in some embodiments, the technology provides a conduit that is biocompatible, flexible, and/or suturable. For example, in some embodiments, the technology provides a conduit comprising porous PCL (e.g., a biocompatible, flexible, and/or suturable conduit). In some embodiments, the technology provides a multichannel array that is hierarchical (e.g., comprising two levels of structure (e.g., a microstructure of scaffold walls and a channel architecture). The technology provides a microchannel array that both increases and/or maximizes the open lumen volume (e.g., by minimizing and/or decreasing microchannel wall thickness) while providing adequate structural support for the material or device despite minimizing and/or decreasing microwall channel thickness.

In some embodiments, porosity is introduced into the microchannel walls. In some embodiments, increasing porosity increases permeability, which provides greater nutrient diffusion throughout the device (e.g., for regenerating axons in some embodiments). However, increasing porosity also decreases the mechanical stiffness and strength of the channel walls. Further, the number and size of channels affects the mechanical integrity of the scaffold and maintaining the open lumen volume.

In some embodiments, microchannel number affects scaffold mechanics for scaffolds comprising synthetic and/or natural polymers. During the development of embodiments of the technology provided herein, experiments were conducted to test the mechanical properties of materials and devices produced according to the technology described herein. For example, materials and devices were tested in transverse compression and three-point bending assays to simulate some typical loading conditions after in vivo implantation.

As described herein, embodiments of the technology provided herein relate to an embossing process that produces micro-features (e.g., 1-1000 μm) in a polymer or composite film while retaining the intrinsic porosity of the starting film (e.g., 0-90 vol %). In some embodiments, the technology comprises providing a pre-formed film, a mold (e.g., heated to approximately 20-200° C. (e.g., (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200° C.)), and, optionally, a compliant backing layer (e.g., a foam); and applying pressure (e.g., using a hydraulic press) to emboss the pre-formed film.

In some embodiments, films, materials, scaffolds, and devices as described herein (e.g., as produced by methods described herein) are provided that further comprise nanoparticles loaded with a therapeutic agent.

Compositions, Materials, and Devices

In some embodiments, the technology provides a material comprising features that are in the range of 1 to 1000 μm (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm). In some embodiments, the technology provides a material comprising features that are in the range of 5 to 500 μm (e.g., 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 μm). In some embodiments, the technology provides a material comprising features that are in the range of 10 to 400 μm (e.g., 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 μm). In some embodiments, the technology provides a material comprising features that are in the range of 1 to 1000 μm and comprising nanoparticles (e.g., pSiNPs) loaded with a therapeutic agent. See, e.g., the experimental examples provided herein.

In some embodiments, the technology provides a material having a porosity (e.g., produced from a film having a porosity) of 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %). In some embodiments, the technology provides a material having a porosity (e.g., produced from a film having a porosity) of 0.1 to 80 vol % (e.g., 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 vol %). In some embodiments, the technology provides a material having a porosity (e.g., produced from a film having a porosity) of 1 to 75 vol % (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 vol %). In some embodiments, the technology provides a material having a porosity (e.g., produced from a film having a porosity) of 0.01 to 90 vol % and comprising nanoparticles (e.g., pSiNPs) loaded with a therapeutic agent. See, e.g., the experimental examples provided herein.

In some embodiments, the technology provides a material produced from a first composition (e.g., a polymer) and a second composition (e.g., an inorganic component). In some embodiments, the technology provides a material comprising a first composition (e.g., a polymer) and a second composition (e.g., an inorganic component). In some embodiments, the technology provides a material comprising a first composition (e.g., a polymer) and a second composition (e.g., an inorganic component) present in said material at a weight % of 0.01 to 70% (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 wt %). In some embodiments, the technology provides a material comprising a first composition (e.g., a polymer) and a second composition (e.g., an inorganic component) present in said material at a weight % of 0.1 to 60% (e.g., 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 wt %). In some embodiments, the technology provides a material comprising a first composition (e.g., a polymer) and a second composition (e.g., an inorganic component) present in said material at a weight % of 1 to 50% (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt %). In some embodiments, the technology provides a material comprising a first composition (e.g., a polymer), a second composition (e.g., an inorganic component) present in said material at a weight % of 0.01 to 70% and comprising nanoparticles (e.g., pSiNPs) loaded with a therapeutic agent. See, e.g., the experimental examples provided herein.

The technology is not limited in the polymer that is used to produce the porous film. In some embodiments, the porous film comprises a polyester (e.g., a polycaprolactone (PCL), a poly(lactide co-glycolide) (PLGA), and combinations thereof). In some embodiments, the porous film comprises a polymer that is a polyester (e.g., polycaprolactone (PCL), poly(lactide co-glycolide) (PLGA), poly(lactic acid), poly(glycolic acid), poly(butylene succinate), poly(ethylene terephthalate), poly(3-hydroxybutyrate-co-3-hydroxyvalerate), poly(butylene terephthalate), poly(hydroxybutyrate), poly(ethylene adipate), poly(hydroxyalkanoate), and/or poly(ethylene naphthalate)), a polyamide, a polypyrrole, a polyethylene, a polyethylene glycol, a chitosan, a poly(vinyl alcohol) (PVA), or combinations of any of the foregoing. In some embodiments, the polymer is chosen based on characteristics related to its behavior in vivo. For example, in some embodiments the polymer is chosen based on biocompatibility. In some embodiments, the polymer is chosen based on degradation and/or stability characteristics (e.g., rate of degradation in vivo).

In some embodiments, the technology provides a material comprising a polymer. In some embodiments, the technology provides a scaffold structure comprising microchannels formed from a biocompatible and/or a biodegradable polymer. In some embodiments, the technology provides a scaffold structure comprising microchannels formed from a biocompatible and/or a biodegradable polymer and comprising nanoparticles (e.g., pSiNPs) loaded with a therapeutic agent. In some embodiments, a biocompatible and/or a biodegradable polymer is a polyester polymer. The technology is not limited in the biodegradable polymer used to produce the materials described herein. For example, in some embodiments, the biodegradable polymer is a polylactic acid, a polycaprolactone (PCL), a polyglycolic acid, a poly(lactide-co-glycolide polymer (PLGA), or a copolymer, derivative, and/or mixtures of any of the foregoing. In some embodiments, the biocompatible and/or biodegradable material is a polycaprolactone (PCL), poly(lactic-co-glycolic acid) (PLGA), or a combination thereof. In some embodiments, a polymer is modified by a chemical and/or a physical method (e.g., cross-linking, heat treatment, photochemical treatment, and/or changes in the chemical or physical environment). In some embodiments, a polymer film is modified at a defined location (e.g., on a surface, on a select portion, in one or more microchannels). In some embodiments, the technology provides control of the extent of modification of a polymer (e.g., a polymer film) to produce materials having a range of characteristics and/or material responses (e.g., by controlling the time of a modification reaction, by controlling the temperature of a modification reaction, by controlling the ratio of a modifying reactant and the polymer (e.g., polymer film)). In some embodiments, polymer modification and/or treatment provides different degradation or release kinetics. In some embodiments, surface alterations, such as differences in hydrophilicity, charge, or other physical properties, facilitate cell adhesion.

In some embodiments, a polymer film is treated with a biofunctional agent or active ingredient (e.g., a drug or other bioactive agent). In some embodiments, a polymer film is designed to have a particular surface property (e.g., surface roughness). In some embodiments, a polymer is functionalized to comprise a surface comprising an exposed moiety, e.g., to guide cellular growth, promote adhesion of cells or tissue, and/or to promote release of biofunctional agents into the surrounding environment.

As described herein and exemplified in the examples, in some embodiments, a polymer film and/or a material comprising a polymer film comprises nanoparticles. In some embodiments, the nanoparticles are silicon nanoparticles (e.g., porous silicon nanoparticles (pSiNPs)). In some embodiments, nanoparticles comprise a therapeutic agent (e.g., a drug (e.g., a small molecule), a peptide, a protein (e.g., an enzyme), a nucleic acid (e.g., an siRNA, an antisense nucleic acid, a CRISPR guide RNA), a lipid, a carbohydrate, etc.). In some embodiments, the technology provides a device (e.g., an implantable device) comprising a polymer film comprising nanoparticles loaded with a therapeutic agent.

In some embodiments, the material comprises a biodegradable material that dissolves, e.g., by physical disintegration, erosion, disruption, and/or dissolution. In some embodiments, the biodegradable material or degradation products thereof are resorbed by a living organism. In some embodiments, degradation of the biodegradable material releases a therapeutic agent (e.g., from a nanoparticle).

In some embodiments, the materials provided herein comprise a biodegradable polymeric material that dissolves or erodes upon exposure to a solvent comprising a high concentration of water, such as blood, serum, growth or culture media, bodily fluids, saliva, and the like. Thus, upon implantation, the material may dissolve or disintegrate into small pieces and, in some embodiments, release a therapeutic agent. For structural scaffold members, the dissolution rate (e.g., a rate at which the material or degradation products thereof is resorbed by surrounding cells) can be designed so that sufficient cellular growth occurs prior to the structure dissolving or disintegrating via the resorption process. In some embodiments, the dissolution rate is designed and/or chosen to provide a therapeutic agent at a particular rate of delivery to a cell, tissue, and/or organ.

In some embodiments, the material is designed to have a degradation time (e.g., the elapsed time for greater than 95, 96, 97, 98, 99, 99.5, 99.9% of the material to degrade) or dissolution rate (e.g., mass of degraded material produced per unit of time) that coincides with an amount of time that permits adequate tissue (e.g., neural tissue) regrowth through the scaffold to a target tissue in a subject. Depending upon the subject and the time needed for recuperation and regeneration of the tissue, by way of non-limiting example, the degradation time may be greater than or equal to about 1 month to less than or equal to about 3 years (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, or 36.0 months), greater than or equal to about 1 month to less than or equal to 1 year (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12.0 months), or greater than or equal to about 1 month to less than or equal to 6 months (e.g., 1.0, 1.5, 2.0, 2.5, 3.0, 3.5, 4.0, 4.5, 5.0, 5.5, or 6.0 months). In this manner, the material (e.g., a scaffold comprising the material) supports and promotes cell growth, cell proliferation, cell differentiation, cell repair, and/or cell regeneration in three-dimensions (e.g., for neural tissue growth).

In some embodiments, the technology provides a material comprising a composite film, e.g., comprising a polymer matrix and a filler material. In some embodiments, the filler material comprises an inorganic component. In some embodiments, the filler material is in the form of, e.g., a fiber, a particle (e.g., a porous particle or a non-porous particle), and/or a nanoparticle. In some embodiments, the technology provides a material comprising a first composition (e.g., a polymer) and a second composition (e.g., a filler (e.g., an inorganic component)). In some embodiments, the material comprises filler material (e.g., an inorganic component) that is, e.g., a metal (titanium, tantalum, aluminum, iron, platinum, gold, silver, and/or palladium), a salt (e.g., NaCl and/or CaCO3), a calcium phosphate, an oxide (e.g., zirconia, alumina, titania, and/or silica), a ceramic, and/or a graphite (e.g., a graphite nanotube and/or graphene). In some embodiments, the technology provides a material comprising a composite film, e.g., comprising a polymer matrix, a filler material, and nanoparticles loaded with a therapeutic agent.

In some embodiments, the technology provides a material comprising a spacer or a porogen (e.g., a gel, an aerogel, particles, a sponge, a foam, a rod or a plurality of rods, fibers, textiles, an aqueous dissolvable material (e.g., a salt), and/or meshes). In some embodiments, the material is produced to comprise the spacer or porogen material and the spacer or porogen material is subsequently removed, minimized, and/or eliminated from the material (e.g., to produce pores, void space, and/or features in the material). Accordingly, embodiments provide methods for removing the spacer or porogen material after the embossing to produce open void spaces in the material. In some embodiments, the technology provides a material comprising a spacer or a porogen (e.g., a gel, an aerogel, particles, a sponge, a foam, a rod or a plurality of rods, fibers, textiles, an aqueous dissolvable material (e.g., a salt), and/or meshes) and nanoparticles loaded with a therapeutic agent.

Embodiments comprise use of a mold (e.g., an embossing block) to emboss a polymer film. In some embodiments, the mold is heated. In some embodiments, the mold comprises a material that withstands the heat and pressure used to emboss the polymer film. In some embodiments, the mold comprises a material that can be machined, etched, etc. to produce surface features in the mold material for introduction of features into the embossed polymer. In some embodiments, the mold comprises a metal (e.g., aluminum). In some embodiments, the mold comprises a polymer (e.g., acetal).

In some embodiments, the technology comprises an embossing method that can be scaled for high throughput manufacturing and/or roll-to-roll processes.

In some embodiments, the technology provides an embossing process in which spacers or void spaces (e.g., having a size of from 1 to 1000 µm (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm)) are incorporated and/or encapsulated between two layers of a polymer or composite film, while retaining the intrinsic porosity of the starting film (e.g., 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %)). Thus, in some embodiments, the technology comprises providing a first film, a second film, a spacer material, a mold (e.g., heated to approximately 20-200° C. (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200° C.)), and, optionally, a compliant backing layer (e.g., a foam); and applying pressure to emboss the first and/or second pre-formed film (e.g., using a hydraulic press). In some embodiments, the spacer material fits between the features of the patterned mold. In some embodiments, the spacer material is physically constrained between the first film and the second film after embossing. In some embodiments, the spacer material comprises, e.g., a gel, an aerogel, particles, a sponge, a foam, a rod or a plurality of rods, fibers, textiles, an aqueous dissolvable material (e.g., a salt), and/or a mesh. In some embodiments, the material is produced to comprise the spacer material and the spacer material is subsequently removed, minimized, and/or eliminated from the material (e.g., to produce pores, void space, and/or features in the material). Accordingly, embodiments provide methods for removing the spacer material after the embossing to produce open void spaces in the material. In some embodiments, the first and/or second film comprises nanoparticles loaded with a therapeutic agent.

In some embodiments, the technology provides a material and/or a device comprising a material. In some embodiments, the technology provides a device made from a polymer or a composite. In some embodiments, the technology provides a device comprising embossed features (e.g., having a size of from 1 to 1000 µm (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm)) and an intrinsic porosity of 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %).

In some embodiments, the technology provides a material comprising nanoparticles loaded with a therapeutic agent and/or a device comprising a material comprising nanoparticles loaded with a therapeutic agent. In some embodiments, the technology provides a device made from a polymer or a composite comprising nanoparticles loaded with a therapeutic agent. In some embodiments, the technology provides a device comprising embossed features (e.g., having a size of from 1 to 1000 µm (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm)) and an intrinsic porosity of 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %) and comprising nanoparticles loaded with a therapeutic agent.

In some embodiments, the technology provides a material produced from an embossed sheet comprising spacer material. In some embodiments, the technology provides a material produced by embossing a polymer sheet comprising spacer material to produce an embossed sheet and rolling the embossed sheet into a cylinder. In some embodiments, the technology further comprises tacking the cylinder at the edge, e.g., using heat, pressure, chemicals, or a combination of the foregoing (e.g., the end of the rolled embossed sheet is temporarily secured to prevent unrolling the rolled embossed sheet so that the rolled embossed sheet can be inserted into a sheath).

In some embodiments, the technology provides a material produced from an embossed sheet comprising nanoparticles loaded with a therapeutic agent and comprising spacer material. In some embodiments, the technology provides a material comprising nanoparticles loaded with a therapeutic agent produced by embossing a polymer sheet comprising nanoparticles loaded with a therapeutic agent and a spacer material to produce an embossed sheet comprising nanoparticles loaded with a therapeutic agent and rolling the embossed sheet into a cylinder. In some embodiments, the technology further comprises tacking the cylinder at the edge, e.g., using heat, pressure, chemicals, or a combination of the foregoing (e.g., the end of the rolled embossed sheet is temporarily secured to prevent unrolling the rolled embossed sheet so that the rolled embossed sheet can be inserted into a sheath).

In some embodiments, the spacer is a wire (e.g., a wire mandrel (e.g., a shaped bar that is placed inside a workpiece to be formed and/or a round object against which material is shaped)). In some embodiments, the spacer (e.g., wire) is removed to create void space. In some embodiments related to producing a material that finds use as a biomedical scaffold (e.g., for tissue growth and/or regeneration), the material comprises features (e.g., channels, pores, ridges, grooves, depressions, ridges, etc.) that are linear features.

In some embodiments, the technology provides a material and/or a device comprising scaffold walls that have interconnected pores (e.g., to allow nutrients and oxygen to permeate laterally through the material (e.g., between microchannels and the scaffold periphery)). In some embodiments, the technology provides a material and/or a device comprising scaffold walls that have interconnected pores (e.g., to allow nutrients and oxygen to permeate laterally through the material (e.g., between microchannels and the scaffold periphery)) and comprising nanoparticles loaded with a therapeutic agent. In some embodiments, pores are produced in a material by using a porogen to displace volume in a polymer as it polymerizes/solidifies. In some embodiments, the porogen is provided in particle form. In some embodiments, the porogen/polymer composition is immersed in a solvent to selectively dissolve the porogen to create pores after polymerization is complete. In some embodiments, the porogen is sodium chloride (NaCl). In some embodiments, the technology comprises reducing the particle size of a porogen. In some embodiments, the technology comprises producing a material using a porogen having reduced porogen dimensions. Thus, in some embodiments, the technology provides a material comprising synthetic polymer scaffold walls comprising numerous interconnected pores having an average pore size of less than or equal to approximately 10 to 50 micrometers (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 micrometers). In some embodiments, the technology provides a material comprising synthetic polymer scaffold walls comprising numerous interconnected pores having an average pore size of less than or equal to approximately 15 to 30 micrometers (e.g., 15, 16, 17, 18, 19, 20, 21, 22, 23, 24, 25, 26, 27, 28, 29, or 30 micrometers). In some embodiments, the technology provides a material comprising synthetic polymer scaffold walls comprising numerous interconnected pores having an average pore size of less than or equal to approximately 17 to 25 micrometers (e.g., 17.0, 17.5, 18.0, 18.5, 19.0, 19.5, 20.0, 20.5, 21.0, 21.5, 22.0, 22.5, 23.0, 23.5, 24.0, 24.5, or 25.0 micrometers).

In some embodiments, the technology relates to methods of making a porous material having microscale and/or nanoscale features. In some embodiments, the technology comprises mixing one or more porogens and a polymeric precursor solution together. In some embodiments, the ratio of the polymer to porogen determines the volume % of the polymer and can be selected based on the targeted porosity and mechanical properties. The polymeric precursor solution may include a polymeric precursor and a first solvent. In some embodiments, the polymeric precursor solution comprises nanoparticles loaded with a therapeutic agent.

In some embodiments, the porogen has an average particle diameter or size of less than or equal to approximately 40 μm, less than or equal to approximately 30 μm, less than or equal to approximately 20 μm, or less than or equal to approximately 10 μm. In some embodiments, the porogen is a material that is brittle and/or soluble in a second solvent and that does not dissolve in the first solvent/polymeric precursor solution. As a rough estimate, a ratio of bulk modulus to the shear modulus indicates the ductile/brittle behavior of a solid. According to Pugh's criterion, a critical value for a transition from brittle to ductile behavior is 1.75. Thus, to facilitate particle reduction via mechanical comminution, porogens may be selected as having Pugh ratios of less than 1.75 (e.g., less than 0.5, 0.6, 0.7, 0.8, 0.9, 1.0, 1.1, 1.2, 1.3, 1.4, 1.5, 1.6, 1.7, or 1.75). In some embodiments, the porogen is sodium chloride, calcium chloride, potassium chloride, a sugar (e.g., sucrose, maltose, lactose, fructose, glucose, galactose, or a combination of the foregoing), or a combination of the foregoing. In some embodiments, the porogen is NaCl. NaCl is a particularly suitable porogen owing to its insolubility in solvents used to dissolve biocompatible polymers (such as polycaprolactone (PCL) and polylactic co-glycolic acid (PLGA)) and its solubility in water, which does not readily dissolve PCL or PLGA.

Some embodiments comprise reducing porogen size. In some embodiments, a mechanical comminution technique is used to mill or pulverize porogen particles (such as NaCl). In some embodiments, the method may thus comprise reducing a particle size of a precursor of the porogen by ball milling the precursor before admixing it with the polymeric solution. In some embodiments, a planetary ball mill is used to mill the porogen to reduce powder particle size. The milling may be for greater than or equal to about 1 minute to less than or equal to several hours (e.g., 1 to 360 minutes (e.g., 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 minutes)), less than or equal to about 2 hours (e.g., less than 5, 10, 15, 20, 25, 30, 35, 40, 45, 50, 55, 60, 65, 70, 75, 80, 85, 90, 95, 100, 105, 110, 115, or 120 minutes), or less than or equal to about 1 hour (e.g., less than 5, 10, 15, 20, 25, 30, 35, 40, 45, 50, 55, or 60 minutes). The speed of the milling may be conducted at 100 RPM to 1000 RPM (e.g., 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 RPM). In some embodiments, the milling is conducted with intervals of mixing alternating with intervals of non-mixing (e.g., rest).

In some embodiments, the technology provides an implantable device. In some embodiments, the implantable device delivers a continuous therapeutic release for up to 60 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days) under physiological conditions. In some embodiments, the implantable device comprises therapeutic-eluting nanoparticles embedded within a polymer matrix. In some embodiments, the implantable device comprises a scaffold having microscale features (e.g., 1-600 μm (e.g., 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 μm)) and high open lumen volume (greater than 50% (e.g., 50, 55, 60, 65, 70, 75, 80, 85, 90, 95, or 100% open lumen volume)). In some embodiments, the implantable device comprises therapeutic-eluting nanoparticles comprising porous silicon. In some embodiments, the implantable device comprises therapeutic-eluting nanoparticles comprising oxidized porous silicon. In some embodiments, the implantable device comprises a polymer film comprising a polyester (e.g., polycaprolactone, poly (lactide co-glycolide), poly (lactic acid), etc.), chitosan, polyethylene, polyethylene glycol, polyamide, polypyrrole, and/or poly(vinyl alcohol).

In some embodiments, the implantable device comprises a polymer film comprising between 0.01 and 99% wt (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% wt) therapeutic-loaded nanoparticles. In some embodiments, the implantable device comprises a polymer film comprising between 0.01 and 50% wt (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% wt) therapeutic-loaded nanoparticles. In some embodiments, the implantable device comprises a polymer film comprising between 1 and 30% wt (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0% wt) therapeutic-loaded nanoparticles. In some embodiments, the implantable device has a porosity of between 0.01 and 99% (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% porosity). In some embodiments, the implantable device has a porosity of between 0.1 and 80% (e.g., 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80% porosity). In some embodiments, the implantable device provides a release rate of the therapeutic that is between 0.01-100,000 ng (e.g., 0.01; 0.02; 0.05; 0.1; 0.2; 0.5; 1; 2; 5; 10; 20; 50; 100; 200; 500; 1000; 2000; 5000; 10,000; 20,000; 50,000; or 100,000 ng) therapeutic released/mg polymer for 10 or more days (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days) under physiological conditions. In some embodiments, the implantable device provides a release rate of the therapeutic that is between 0.1-10,000 ng (e.g., 0.1; 0.2; 0.5; 1; 2; 5; 10; 20; 50; 100; 200; 500; 1000; 2000; 5000; or 10,000 ng) therapeutic released/mg polymer for 10 or more days (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days) under physiological conditions. In some embodiments, the implantable device provides a release rate of the therapeutic that is between 1-1000 ng (e.g., 1; 2; 5; 10; 20; 50; 100; 200; 500; or 1000 ng) therapeutic released/mg polymer for 10 or more days (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days) under physiological conditions.

In some embodiments, the implantable device comprises a first region contiguous in porosity and structure with a second region, wherein the first region comprises a first therapeutic and the second region comprises a second therapeutic. In some embodiments, the implantable device comprises a first region contiguous in porosity and structure with a second region, wherein the first region comprises a first concentration of a therapeutic and the second region comprises a second concentration of said therapeutic (e.g., including a concentration of zero (e.g., comprises no therapeutic)). The technology is not limited to comprising a first and second region. Thus, in some embodiments, the technology provides an implantable device comprising 1, 2, 3, 4, 5, or more regions (e.g., 1, 2, 3, 4, 5, 6, 7, 8, 9, 10, 11, 12, 13, 14, 15, 16, 17, 18, 19, or 20 regions) that are contiguous in porosity and/or structure. Embodiments provide that each of the 1, 2, 3, 4, 5, or more regions (e.g., 1, 2, 3, 4, 5, 6, 7, 8, 9, 10, 11, 12, 13, 14, 15, 16, 17, 18, 19, or 20 regions) may or may not comprise a therapeutic. Embodiments provide that each of the 1, 2, 3, 4, 5, or more regions (e.g., 1, 2, 3, 4, 5, 6, 7, 8, 9, 10, 11, 12, 13, 14, 15, 16, 17, 18, 19, or 20 regions) that comprise a therapeutic may comprise the same or different therapeutic and may comprise the therapeutic at different concentrations.

Accordingly, some embodiments provide an implantable device comprising multiple therapeutic delivery sites. In some embodiments, the therapeutic delivery sites comprise the same therapeutic (e.g., present at the same or at different concentrations) and in some embodiments the therapeutic delivery sites comprise different therapeutics. In some embodiments, the implantable device comprises multiple therapeutic delivery sites that release the loaded therapeutics substantially and/or effectively simultaneously, in a temporal sequence, in a spatial sequence, and/or any combination of the foregoing. In some embodiments, implantable devices are produced from two or more polymer films as described herein, wherein one or more of the polymer films comprises therapeutic-eluting nanoparticles. In some embodiments, the films are embossed with a spacer (e.g., a wire mandrel) that is subsequently removed to create open void space). In some embodiments, the films are rolled into a cylinder. In some embodiments, the films are rolled and tacked at the edge (e.g., using heat, pressure, chemicals or a combination of the three).

Methods

Related embodiments provide methods for producing a polymer film and/or a device comprising a polymer film. In some embodiments, methods comprise obtaining and/or providing a polymer material. In some embodiments, methods comprise dissolving a polymer material in a solvent (e.g., an organic solvent, an aqueous solvent). In some embodiments, methods comprise obtaining and/or producing a solution of a polymer material in a solvent. In some embodiments, methods comprise obtaining and/or providing a solution of a polymer comprising approximately 0.1% wt % of the polymer to approximately 50 wt % of the polymer (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt %). In some embodiments, the methods comprise obtaining, providing, and/or producing a polymer material comprising nanoparticles loaded with a therapeutic agent. See, e.g., U.S. Pat. No. 7,713,778, incorporated herein by reference.

In some embodiments, methods comprise adding a porogen to a polymer solution. In some embodiments, methods comprise obtaining, producing, and/or providing a slurry comprising a polymer solution and a porogen. In some embodiments, methods comprise obtaining, producing, and/or providing a slurry comprising a polymer solution, a porogen, and nanoparticles loaded with a therapeutic agent. Some embodiments comprise steps for loading nanoparticles with a therapeutic agent. See, e.g., the examples herein. See also, e.g., U.S. Pat. No. 7,713,778, incorporated herein by reference.

In some embodiments, methods comprise physically changing the porogen prior to adding it to the polymer solution (e.g., by machining the porogen). For example, in some embodiments, methods comprise screening, milling, crushing, and/or otherwise machining a porogen to produce a porogen of a particular size or particular range of sizes. In some embodiments, the porogen has a size after machining of approximately 0.1 to 100 µm (e.g., 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µm). In some embodiments, the porogen has a range of sizes where the distribution of the sizes has a peak, maximum, median, mean, and/or mode of the distribution of sizes is approximately 0.1 to 100 µm (e.g., 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µm).

In some embodiments, machining the porogen comprises using a ball mill. In some embodiments, machining the porogen comprises ball milling the porogen at approximately 50 to 1000 rpm (e.g., 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 rpm). In some embodiments, machining the porogen comprises ball milling the porogen for approximately 20 to 600 minutes (e.g., 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600 minutes). In some embodiments, machining the porogen comprises machining the porogen for a period of time (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0 minutes) and not machining the porogen for a period of time (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0 minutes). In some embodiments, the periods of machining the porogen and not machining the porogen alternate a number of times during the ball milling, e.g., the ball milling comprises intervals of ball milling (for a period of time as described above) each followed by an interval of not ball milling (for a "rest" period of time as described above).

Embodiments comprise providing slurries comprising polymer and porogen in a range of ratios. For example, embodiments provide a slurry comprising a solubilized polymer solution and a porogen at a ratio of approximately 5 vol %/95 vol % polymer to porogen to 95 vol %/5 vol % polymer to porogen (e.g., a solubilized polymer solution comprising porogen at 5 to 95 vol % (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 vol %).

Embodiments comprise providing slurries comprising polymer and porogen in a range of ratios and further comprising nanoparticles loaded with a therapeutic agent. For example, embodiments provide a slurry comprising a solubilized polymer solution and a porogen at a ratio of approximately 5 vol %/95 vol % polymer to porogen to 95 vol %/5 vol % polymer to porogen (e.g., a solubilized polymer solution comprising porogen at 5 to 95 vol % (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 vol %) and further comprising between 0.01 and 99% wt (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% wt) therapeutic-loaded nanoparticles, between 0.01 and 50% wt (e.g., 0.01, 0.02, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% wt) therapeutic-loaded nanoparticles, or between 1 and 30% wt (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0% wt) therapeutic-loaded nanoparticles.

In some embodiments, the slurry comprising solubilized polymer and porogen (and, optionally, therapeutic-loaded nanoparticles) is mixed. In some embodiments, mixing comprises use of a ball mill to mix the slurry. In some embodiments, mixing the slurry comprises mixing for 1 to 600 minutes (e.g., 1, 2, 3, 4, 5, 6, 7, 8, 9, 10, 15, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600 minutes). In some embodiments, mixing the slurry comprises mixing the slurry for a period of time (e.g., 0.25, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0 minutes) and not mixing the slurry for a period of time (e.g., 0.25, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0 minutes). In some embodiments, the periods of mixing the slurry and not mixing the slurry alternate a number of times during mixing, e.g., the mixing comprises intervals of mixing (for a period of time as described above) each followed by an interval of not mixing (for a "rest" period of time as described above).

In some embodiments, methods comprise producing a polymer film from the slurry comprising the polymer and porogen (and, optionally, further comprising therapeutic-loaded nanoparticles). In some embodiments, producing a polymer film comprises casting the slurry to produce a polymer film comprising porogen. In some embodiments, producing a polymer film comprises spreading the slurry on a substrate to produce a polymer film comprising porogen. In some embodiments, producing a polymer film comprises drying a slurry spread on a substrate to produce a polymer film comprising porogen. In some embodiments, the final dry thickness of the polymer film is approximately 10 to 1000 μm (e.g., 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm). In some embodiments, embodiments comprise removing the dried polymer film from the substrate (e.g., using a wetting solution (e.g., an alcohol (e.g., ethanol)) or water). In some embodiments, a polymer film is calendered to produce a finished film. In some embodiments, calendering the polymer film produces a polymer film having a thickness of (e.g., 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm).

In some embodiments, methods comprise removing porogen from a polymer film comprising porogen (and, optionally, further comprising therapeutic-loaded nanoparticles). In some embodiments, removing porogen comprises contacting (e.g., immersing, soaking, washing) the polymer film comprising porogen with a solvent that dissolves the porogen but that does not dissolve the polymer (e.g., an aqueous solution). In some embodiments, the polymer film comprising the porogen is contacted (e.g., immersed, soaked, washed) for 10 minutes to 10 hours (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, or 600 minutes). In some embodiments, washing the polymer film comprising porogen comprises changing (e.g., replacing) the solvent that dissolves the porogen but that does not dissolve the polymer (e.g., an aqueous solution) one or more times with fresh solvent that dissolves the porogen but that does not dissolve the polymer (e.g., an aqueous solution).

In some embodiments, the methods produce a polymer film having a porosity greater than 50 vol %. In some embodiments, the methods produce a polymer film having a porosity greater than 60 vol % (see Examples below). In some embodiments, the methods produce a material having a porosity (e.g., produced from a film having a porosity) of 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %). In some embodiments, the methods produce a material having a porosity (e.g., produced from a film having a porosity) of 0.1 to 80 vol % (e.g., 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 vol %). In some embodiments, the methods produce a material having a porosity (e.g., produced from a film having a porosity) of 1 to 75 vol % (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 vol %). See, e.g., the experimental examples provided herein. In some embodiments, the methods produce a polymer film and/or material having the aforementioned porosities and further comprising therapeutic-loaded nanoparticles.

Figure 5A:
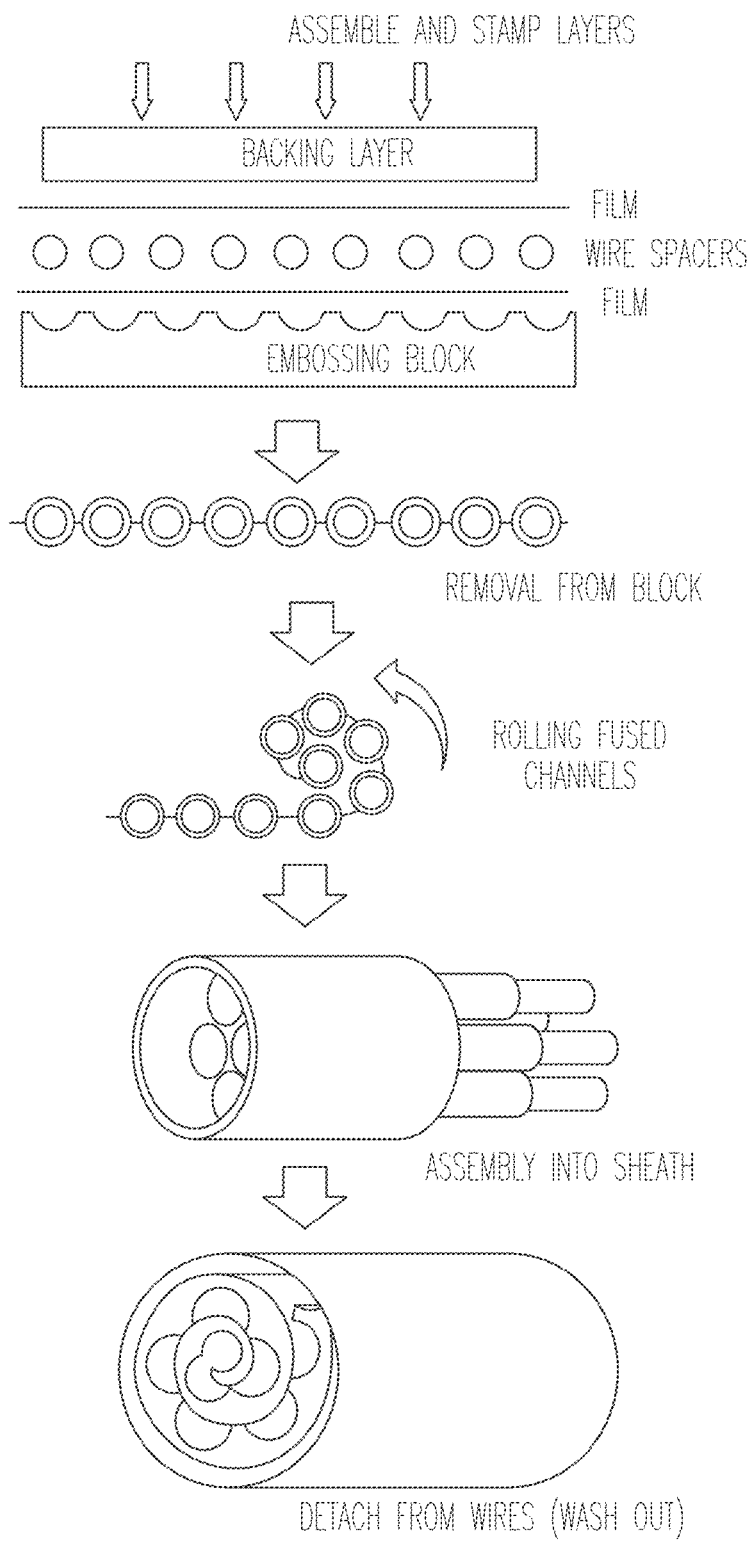
FIG. 5A shows a schematic drawing of an embodiment of a method described herein. The method described in FIG. 5A comprising steps of assembling polymer film, spacers, and an embossing block; embossing the polymer film; removing the embossed film from the embossing block; rolling the embossed polymer film; assembling the rolled polymer film into a sheath; and removing the spacers.
Figure 5B:
FIG. 5B is a micrograph showing a side view of an embossing block comprising microscale features.
Figure 5C:
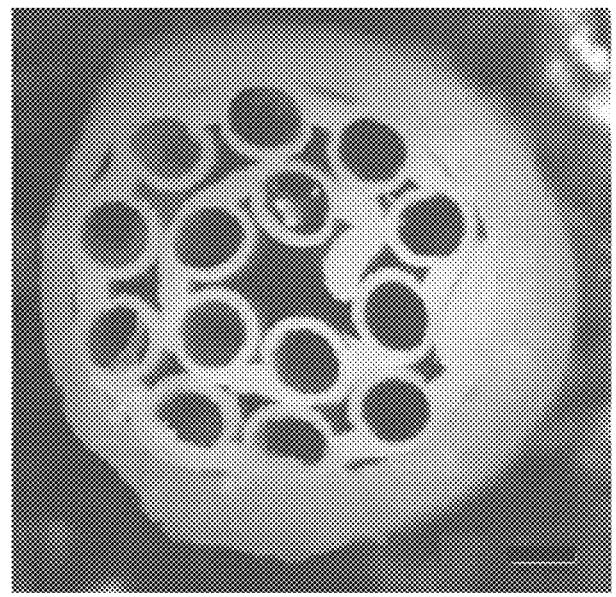
FIG. 5C is a micrograph showing a cross-section of a device produced according to an embodiment of the technology described herein. The device comprises void spaces to provide linear microchannels. The scale bar in FIGS. 5B and 5C indicates a distance of 250 µm.

In some embodiments, methods comprise embossing a polymer film (e.g., a porous polymer film as described herein, a porous polymer film comprising therapeutic-loaded nanoparticles as described herein, and/or as produced according to embodiments of methods described herein) (see, e.g., FIG. 1; FIG. 5, panel (a); and/or FIG. 9A). In some embodiments, embossing a polymer film comprises providing a polymer film as described above and/or produced according to a method described above. In some embodiments, embossing a polymer film comprises obtaining, producing, and/or providing a polymer film as described herein (e.g., having an intrinsic porosity of from 0.01 to 90 vol %, 0.1 to 80 vol %, 1 to 75 vol %, greater than 50 vol %, or greater than 60 vol %; providing an embossing block (e.g., a mold) comprising features (e.g., linear features) on a surface (e.g., a surface configured to contact a polymer film). In some embodiments, methods comprise embossing a plurality of polymer films arranged so that each film overlaps an adjacent film by approximately 1 mm (e.g., 0.8, 0.85, 0.9, 0.95, 1, 1.05, 1.1, 1.15, or 1.2 mm). In some embodiments, embossing a polymer film comprises providing a plurality of polymer films as described above and/or produced according to a method described above. In some embodiments, embossing a plurality of polymer films comprises obtaining, producing, and/or providing a plurality of polymer films as described herein.

In some embodiments, the embossing block comprises features that are in the range of 1 to 1000 μm (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm). In some embodiments, the embossing block comprises features that are in the range of 5 to 500 μm (e.g., 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 μm). In some embodiments, the embossing block comprises features that are in the range of 10 to 400 μm (e.g., 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 μm). See, e.g., the experimental examples provided herein.

In some embodiments, embossing comprises pressing a polymer film as described herein (e.g., comprising an intrinsic porosity and, optionally, comprising therapeutic-loaded nanoparticles) or a plurality of adjacent, overlapped polymer films against an embossing mold. In some embodiments, pressing the polymer film against the embossing mold comprises pressing the polymer film against the embossing mold using a pressure of approximately 0.1 to 10 metric tons of force (e.g., 0.1, 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 metric tons of force). In some embodiments, the embossing block is heated to a temperature of approximately 20-200° C. (e.g., (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200° C.). In some embodiments, a hydraulic press is used to press the polymer film against the embossing mold.

In some embodiments, a backing layer is placed between the source of pressure and the polymer film. In some embodiments, the backing layer comprises a foam, gel, or other compressible material.

In some embodiments, methods comprise obtaining, producing, and/or providing a spacer or a plurality of spacers. The technology is not limited in the shape of the spacer. For example, in some embodiments, the spacer is a rod, sphere, prism, sheet, slab, or other three-dimensional shape. In some embodiments, the spacer has one, two, and/or three dimensions that is/are in the range of 1 to 1000 μm (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm). In some embodiments, the spacer has a shape that is complementary to a feature on the embossing block (e.g., the spacer has a similar shape as a feature on the embossing block and, in some embodiments, the spacer fits within a feature on the embossing block).

The technology is not limited in the material that comprises the spacer. In some embodiments, the spacer comprises a metal. In some embodiments, the spacer comprises a polymer. In some embodiments, the spacer comprises a glass, ceramic, or graphite material.

In some embodiments, embossing comprises placing one or more spacers in contact with the polymer sheet prior to pressing the polymer film against the embossing mold. In some embodiments, embossing comprises placing one or more spacers in contact with the polymer sheet during pressing the polymer film against the embossing mold. In some embodiments, the spacer is placed between the polymer film and the embossing mold. In some embodiments, the spacer is placed between the polymer film and the source of the pressure. In some embodiments, the spacer is treated (e.g., coated, washed, stripped, functionalized, etc.) prior to placing in contact with the polymer film. In some embodiments, the spacer is coated with a polymer.

In some embodiments, a plurality of spacers is used (e.g., methods comprise contacting the polymer film with a plurality of spacers arranged to contact the polymer film (e.g., to produce a pattern of features in the polymer film after embossing)). In some embodiments, a plurality of spacers is arranged in intervals along one dimension (see, e.g., FIG. 3, panel (a) and panel (b); see, e.g., FIG. 5, panel (a)). In some embodiments, a plurality of spacers is arranged in intervals along two dimensions (e.g., an array). In some embodiments, a plurality of spacers comprises 1 to 100 spacers (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 spacers). In some embodiments, a plurality of spacers comprises 1 to 1000 spacers.

In some embodiments, methods comprise providing, producing, and/or obtaining a first polymer film and a second polymer film. In some embodiments, methods comprise placing the first polymer film on the embossing block and embossing the first polymer film as described above (e.g., using a pressure of approximately 0.1 to 10 metric tons of force (e.g., 0.1, 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 metric tons of force). Then, in some embodiments, methods comprise relieving the pressure and then placing a plurality of spacers on the first polymer film, placing the second polymer film on the plurality of spacers, and applying pressure to the first polymer film, spacers, and second polymer film (e.g., as described herein and below). In some embodiments, methods comprise placing the first polymer film on the embossing mold, placing a plurality of spacers on the first polymer film, and placing the second polymer film on the plurality of spacers (see, e.g., FIG. 5, panel (a)). In some embodiments, the embossing mold and/or blocks used to apply pressure to the embossing mold and polymer films have been preheated to a temperature of approximately 20-200° C. (e.g., (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200° C.). In some embodiments, a backing layer is placed in contact with the first polymer film and/or the second polymer film. Embodiments further comprise pressing the first polymer film, the spacers, and the second polymer film against the embossing mold to produce a material comprising linear channels occupied by the spacers. In some embodiments, pressing the first polymer film, the spacers, and the second polymer film against the embossing mold comprises use of a hydraulic press. In some embodiments, pressing the first polymer film, the spacers, and the second polymer film against the embossing mold comprises applying a pressure of approximately 0.1 to 10 metric tons of force (e.g., 0.1, 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 metric tons of force).

Embodiments provide that the polymer material retains intrinsic porosity after embossing. In some embodiments, the spacers are removed to produce a material comprising linear channels and retaining the intrinsic porosity of the polymer material. In some embodiments, the linear channels are essentially, substantially, or effectively parallel to each other. Accordingly, embodiments of the methods produce a polymer material comprising: 1) wall thicknesses of less than 100 µm (e.g., less than approximately 100, 95, 90, 85, 80, 75, 70, 65, 60, 55, 50, 45, 40, 35, 30, 25, 20, 15, or 10 µm); 2) reproducible and homogeneous microscale features and/or channels (e.g., features having a size in the range of approximately 1 µm to 1 mm (e.g., approximately 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm)); and/or 3) an interconnecting porosity of 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %).

In some embodiments, the technology provides methods of producing a device comprising a polymer material. In particular, methods comprise producing a device comprising a polymer material comprising microscale features and/or channels (e.g., features having a size in the range of approximately 1 µm to 1 mm (e.g., approximately 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm)); and/or an interconnecting porosity of 0.01 to 90 vol % (e.g., 0.01, 0.02, 0.03, 0.04, 0.05, 0.06, 0.07, 0.08, 0.09, 0.10, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 vol %).

In some embodiments, methods comprise providing, producing, and/or obtaining an embossed polymer material as described herein (e.g., comprising microchannels and an intrinsic porosity). In some embodiments, the embossed polymer material comprises a porogen. In some embodiments, the embossed polymer material has had a porogen removed from it. In some embodiments, the embossed polymer material comprises one or more spacers. In some embodiments, the embossed polymer material has had spacers removed from it. In some embodiments, methods comprise producing a device from the embossed polymer material. For example, some embodiments comprise rolling the embossed polymer material into a cylinder shape (see, e.g., FIG. 5, panel (a)). In some embodiments, methods comprise rolling the embossed polymer material into a prism shape (e.g., having a triangular, quadrilateral, pentagonal, hexagonal, etc. end shape). In some embodiments, methods comprise folding the embossed polymer material onto itself one or more times (e.g., in a serpentine pattern). In some embodiments, the device has a diameter of approximately 0.1 to 10 mm (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mm).

In some embodiments, the rolled and/or folded device is pressed in a pressing mold. Accordingly, in some embodiments, methods comprise pressing a device as described herein in a pressing mold. In some embodiments, the pressing mold is preheated to a temperature of approximately 20-200° C. (e.g., (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200° C.). In some embodiments, a pressure of 0.1 to 10 metric tons of force (e.g., 0.1, 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 metric tons of force) is applied to the pressing mold.

In some embodiments, methods comprise washing a device to remove porogen. In some embodiments, methods comprise removing porogen from a device comprising porogen (e.g., comprising a polymer comprising a porogen). In some embodiments, removing porogen comprises contacting (e.g., immersing, soaking, washing) the device comprising porogen with a solvent that dissolves the porogen but that does not dissolve the polymer of the device (e.g., an aqueous solution). In some embodiments, the device comprising the porogen is contacted (e.g., immersed, soaked, washed) for 10 minutes to 10 hours (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, or 600 minutes). In some embodiments, washing the device comprising porogen comprises changing (e.g., replacing) the solvent that dissolves the porogen but that does not dissolve the polymer of the device (e.g., an aqueous solution) one or more times with fresh solvent that dissolves the porogen but that does not dissolve the polymer (e.g., an aqueous solution). In some embodiments, methods comprise removing spacers from a device to provide channels in the device. In some embodiments, methods comprise inserting the device into a sheath. In some embodiments, methods comprise drying the device and/or polymer material.

Therapeutics

Embodiments of the technology relate to delivery of a therapeutic agent. Thus, in some embodiments, the technology contemplates the use of any biologically active therapeutic agent (e.g., for loading into nanoparticles and for incorporation into the films, materials, and devices described herein). As used herein, a therapeutic agent is a substance that may have medicinal, intoxicating, performance enhancing, or other effects when taken or put into an organism (e.g., a human body or the body of another animal), such as a chemical substance used in the treatment, cure, prevention, or diagnosis of disease or used otherwise to modulate (e.g., to enhance) physical or mental well-being. Such agents include, but are not limited to, a toxin, an enzyme, an antibody (or fragment or derivative of an antibody), an aptamer, an inhibitor, a small molecule, a metabolite, a cofactor, a vitamin, a hormone, a neurotransmitter, a stimulant, a modulator of neurotransmitters, (e.g., a cholinergic, a dopaminergic, a serotonergic), antagonists and agonists of biological targets, etc. The therapeutic agent may be a natural compound, an analog of a natural compound, or a synthetic compound. Particular exemplary therapeutic agents include, but are not limited to, e.g., statins, opioids, enzyme inhibitors, analgesics, stimulants, benzodiazepines, steroids, receptor antagonists, sedatives, agonists, calcium channel blockers, antidepressants, enzymes, hormones, narcotics, barbiturates, antibiotics, anabolic steroids, dietary supplements, beta blockers, depressants, proteins, diuretics, antipsychotics, calcium, insulin, anticonvulsants, vitamins, hallucinogens, nonsteroidal anti-inflammatory drugs, anti-inflammatory drugs, ACE inhibitors, anesthetics, anti-diabetic medications, antiviral drugs, angiotensin II receptor blockers, chemotherapeutic agents, antibodies, hypnotics, anticoagulants, psychoactive drugs, anxiolytics, proton-pump inhibitors, antiemetics, antihypertensive drugs, estrogen, corticosteroids, vaccines, anticholinergic drugs, and/or antiarrhythmic agents.

Uses

In some embodiments, the technology finds use in tissue engineered scaffold technology. For example, in some embodiments, the technology finds use in nerve repair. In some embodiments, the technology provides a scaffold comprising microchannels (e.g., comprising aligned, high aspect ratio features). In some embodiments, the technology provides a flexible scaffold. In some embodiments, the technology provides a scaffold having porous scaffold walls. In some embodiments, the technology provides a scaffold having an increased open lumen volume relative to present technologies. In particular, embodiments of the present technology provide materials comprising an open lumen volume of 60 vol % or more (e.g., at least 60, 61, 62, 63, 64, 65, 66, 67, 68, 69, 70, 71, 72, 73, 74, 75, 76, 77, 78, 79, or 80 vol %) in contrast to present technologies (e.g., dip coating) that have been limited to producing materials having an open lumen volume of less than 52 vol % (e.g., less than 52, 51, 50, 49, 48, 47, 46, 45, 44, 43, 42, 41, 40, 39, 38, 37, 36, 35, 34, 33, 32, 31, or 30 vol % or less). For example, some previous technologies are limited to producing materials having an open lumen volume of between 45 and 52 vol % (see, e.g., Pawelec et al. (2019) "The mechanics of scaling-up multichannel scaffold technology for clinical nerve repair" Journal of the Mechanical Behavior of Biomedical Materials 91: 247-254, incorporated herein by reference).

Accordingly, embodiments of the present technology improve tissue (e.g., nerve) regeneration relative to present technologies. In particular, the present technology provides a material and/or scaffold having an increased open lumen volume relative to present technologies, thus providing an increased volume available for regenerating tissue (e.g., nerve tissue). See, e.g., Pawelec et al. (2018) "Microstructure and in vivo characterization of multi-channel nerve guidance scaffolds" Biomed. Mater 13: 044104, incorporated herein by reference in its entirety.

In some embodiments, the technology finds use as a catalyst and/or to produce a catalyst. For example, present designs for flow catalysts, such as those used in automotive exhaust systems, rely on mass and heat transfer. However, both of these transfer processes are not efficient in current state-of-the-art honeycomb structures. Recently, porous open-cell catalysts have been produced that have both greater surface/volume ratios than previous catalysts, thus increasing mass transfer and improving catalysis, while also comprising amounts of expensive catalysis reagents (e.g., platinum) that are less than 25% of the amounts used to produce previous catalysts. See, e.g., Papetti et al. (2018) "Additive manufactured open cell polyhedral structures as substrates for automotive catalysts" Int. J. Heat and Mass Transfer 126: 1035-1047, incorporated herein by reference in its entirety.

Both the amount of porosity and the characteristics of the porous structure itself (e.g., strut size, strut shape) influence effective transfer of heat and mass in reactions. See, e.g., Ulpts et al. (2018) "3D characterization of gas phase reactors with regularly and irregularly structured monolithic catalysts by NMR imaging and modeling" Catalysis Today 310: 176-186; and Papetti supra, each of which is incorporated herein in its entirety. These parameters of the porous structures are difficult to control in most manufacturing methods. In contrast, embodiments of the embossing technology provided herein provides improved control of feature size, feature shape, and/or surface/volume ratio within an open structure. In addition, while extant open-cell structures and foams have potential, there is no cost-effective way to manufacture foams from suitable materials, including metals and ceramic oxides. See, e.g., Monno et al. (2018) "Cost-Efficient Aluminum Open-Cell Foams: Manufacture, Characterization, and Heat Transfer Measurements" Adv. Eng. Mater. 20: 1701032, incorporated herein by reference in its entirety.

Embodiments of the technology provided herein, e.g., compositions produced by the embossing methods described herein, provide materials that have a defined open-cell structure and that are produced from a variety of materials and/or materials systems. Further, embodiments of the methods described herein are amenable to high-throughput manufacturing methods for scale-up to commercially relevant production. Another advantageous feature of the technology provided herein is that some embodiments comprise functionalizing a surface prior to forming a structure, e.g., to provide a homogeneous coating of expensive reactants (e.g., platinum) on the surface, which further reduces the amount of catalysis reagents used in the production of the catalyst.

In some embodiments, the technology provides a technology for delivery of a therapeutic agent (e.g., to provide a sustained release of a therapeutic agent over time). In some embodiments, the technology provides a delivery vehicle that provides localized release of a therapeutic agent over time. In some embodiments, the technology provides a delivery vehicle that targets release of a therapeutic agent to a particular organ, tissue, and/or cell type. Furthermore, in some embodiments, the technology provides a delivery technology that does not have an initial "burst phase" release of therapeutic agent where a large amount of therapeutic agent (e.g., greater than 25, 30, 35, 40, 45, 50, 55, 60, 65, 70, 75, 80, or 85% or more of the therapeutic agent initially provided by the device) is released over a small time span (e.g., a time that is less than 25, 20, 19, 18, 17, 16, 15, 14, 13, 12, 11, 10, 9, 8, 7, 6, 5, 4, 3, 2, or 1% of the total time of release of the therapeutic agent by the delivery technology) shortly after placing the device in a subject. In some embodiments, the therapeutic agent is a drug (e.g., small molecule), a peptide, a nucleic acid (e.g., siRNA, antisense RNA, guide RNA for CRISPR), an enzyme, a lipid, or a carbohydrate).

In some embodiments, a delivery device comprises a porous material comprising microscale and/or nanoscale features and embedded nanoparticles (e.g., porous silicon nanoparticles) comprising a therapeutic agent. In some embodiments, porous silicon nanoparticles (pSiNPs) trap molecules of a therapeutic agent in the nanoparticle pores and retain the therapeutic agent in an active state for days, weeks, months, or years before release of the therapeutic agent. While pSiNPs typically release a therapeutic agent over a time of approximately 1 to 2 days, providing a layer of polymer around pSiNPs slows the release of therapeutic agent, e.g., providing a sustained release over 1-7 days (e.g., 1, 2, 3, 4, 5, 6, or 7 days), 1-4 weeks (e.g., 1, 2, 3, or 4 weeks), and/or 1-12 months (1, 2, 3, 4, 5, 6, 7, 8, 9, 10, 11, or 12 months). See, e.g., Zuidema et al. (2018) "Oriented Nanofibrous Polymer Scaffolds Containing Protein-Loaded Porous Silicon Generated by Spray Nebulization" Adv. Mater. 30: 1706785; Moller et al. (2016) "Highly efficient siRNA delivery from core-shell mesoporous silica nanoparticles with multifunctional polymer caps" Nanoscale 8(7): 4007-19; Xu et al. (2015) "Smart Porous Silicon Nanoparticles with Polymeric Coatings for Sequential Combination Therapy" Mol. Pharm. 12(11): 4038-4047; Irani (2015) "A novel pressed porous silicon-polycaprolactone composite as a dual-purpose implant for the delivery of cells and drugs to the eye" Experimental Eye Research 139: 123-131; Nan et al. (2014) "Porous silicon oxide-PLGA composite microspheres for sustained ocular delivery of daunorubicin" Acta Biomater. 10(8): 3505-3512; Coffer (2014) "Porous silicon and related composites as functional tissue engineering scaffolds" in Porous Silicon for Biomedical Applications (Santos, ed.), pp. 470-485; Meng (2011) "Use of Size and a Copolymer Design Feature To Improve the Biodistribution and the Enhanced Permeability and Retention Effect of Doxorubicin-Loaded Mesoporous Silica Nanoparticles in a Murine Xenograft Tumor Model" ACS Nano 5(5): 4131-4144; Bonanno and Segal (2011) "Nanostructured porous silicon-polymer-based hybrids: from biosensing to drug delivery" Nanomedicine 6(10): 1755-1770; Serda et al. (2010) "Cellular association and assembly of a multistage delivery system" Small 6(12): 1329-1340; Perelman et al. (2010) "Preparation and Characterization of a pH- and Thermally Responsive Poly(N-isopropylacrylamide-co-acrylic acid)/Porous SiO(2) Hybrid" Adv. Funct. Mater. 20(5): 826-833; Kashanian et al. (2010) "Evaluation of mesoporous silicon/polycaprolactone composites as ophthalmic implants" Acta Biomater. 6(9): 3566-3572; De Stefano et al. (2010) "A nanostructured hybrid material based on polymer infiltrated porous silicon layer" Appl. Phys. A-Mater. Sci. Process. 98(3): 525-530; Xia et al. (2009) "Polyethyleneimine Coating Enhances the Cellular Uptake of Mesoporous Silica Nanoparticles and Allows Safe Delivery of siRNA and DNA Constructs" ACS Nano 3(10): 3273-3286; Wu and Sailor (2009) "Chitosan Hydrogel-Capped Porous SiO2 as a pH-Responsive Nano-Valve for Triggered Release of Insulin" Adv. Funct. Mater. 19: 733-741; McInnes and Voelcker (2009) "Silicon-polymer hybrid materials for drug delivery" Future Med. Chem. 1(6): 1051-1074: McInnes et al. (2009) "New biodegradable materials produced by ring opening polymerisation of poly(L-lactide) on porous silicon substrates" J. Colloid Interface Sci. 332 (2): 336-344; Whitehead et al. (2008) "High-porosity poly (epsilon-caprolactone)/mesoporous silicon scaffolds: Calcium phosphate deposition and biological response to bone precursor cells" Tissue Engineering Part A 14(1): 195-206; Anglin et al. (2008) "Porous silicon in drug delivery devices and materials" Adv. Drug Deliv. Rev. 60(11): 1266-1277: Coffer et al. (2007) "Degradable electrospun porous silicon-biopolymer composites for orthopedic tissue engineering" ABSTR PAP AM CHEM S 2007: 233; Mukherjee et al. (2006) "Biorelevant mesoporous silicon/polymer composites: directed assembly, disassembly, and controlled release" Biomed. Microdevices 8(1): 9-15; Coffer et al. (2005) "Porous silicon-based scaffolds for tissue engineering and other biomedical applications" Phys. Status Solidi A-Appl. Mat. 202(8): 1451-1455; Li et al. (2003) "Polymer Replicas of Photonic Porous Silicon for Sensing and Drug Delivery Applications" Science 299(5615): 2045-2047, each of which is incorporated herein by reference. See also U.S. Pat. No. 7,713,778, incorporated herein by reference.

In some embodiments, the thickness of the polymer layer and/or the degradation properties of the polymer itself control the release of the therapeutic agent. One of skill in the art can choose and/or test polymer and polymer thickness to provide the desired release characteristics.

The technology provides the advantage of localized (in contrast to systemic) release of therapeutic agent. The technology also provides the advantage of incorporating increased amounts of therapeutic agent per mass of polymer relative to previous devices.

In some embodiments, the technology provides homogeneous polymer comprising embedded pSiNPs and related devices for use in regenerative medicine. Embodiments of the technology provide delivery devices that have a high open lumen volume and increased permeability. Embodiments of the technology provide delivery devices that have sufficient mechanical stability to be implanted by surgeons and integrate with tissue while delivering a therapeutic payload. Embodiments of the technology provide delivery devices that comprise a spatial variation in the concentration and/or amount of a therapeutic agent over the surface of the device to provide spatially patterned release of therapeutic agent. Embodiments of the technology provide delivery devices that provide temporal control of the release of therapeutic agent. Accordingly, spatial and temporal tuning provides devices that deliver one or more therapeutics to different areas of a lesion site within the same implant, with release profiles tuned to the specific stage of the healing process where they can be most beneficial.

The polymer film delivery vehicle described herein provides several advantages relative to use of a pSiNP alone for delivery of a therapeutic agent. For example, embodiments of the technology comprise a range of biocompatible polymeric materials (e.g., polycaprolactone (PCL) and/or poly(lactide-co-glycolide) (PLGA)) and can release therapeutic agents from days to weeks to months without a burst phase. In some embodiments, the technology provides a delivery vehicle having a release time can be tuned, e.g., by changing polymer thickness, polymer degradation, amount of pSiNPs, pSiNP size, pSiNP pore size, and/or porosity. In some embodiments, the technology provides a delivery vehicle that delivers high amounts of therapeutic per mass polymer (e.g., greater than 1 ng of a therapeutic agent/mg polymer). In some embodiments, the technology provides a technology for the localized release of a therapeutic agent. In some embodiments, the delivery vehicle provides an implantable device that is specific for the medical intervention needed by a subject. In some embodiments, the delivery vehicle extends the bioactive life of the therapeutic agent (e.g., by slowing, eliminating, and/or minimizing denaturing of biomolecules). In some embodiments, the delivery vehicle provides spatial and temporal control of delivery of the therapeutic agent.

Although the disclosure herein refers to certain illustrated embodiments, it is to be understood that these embodiments are presented by way of example and not by way of limitation.

EXAMPLES

During the development of embodiments of the technology, experiments were conducted to produce and test an embossed polymer sheet with linear features and intrinsic porosity, produce and test a material comprising an embossed polymer, and to produce devices comprising an embossed polymer.

Materials and Methods

Materials preparation. A slurry was produced using poly(ε-caprolactone) (Sigma Aldrich, number average molar mass: 80 kDa; PCL). The PCL was solubilized in chloroform at a concentration of 3 wt %. Porosity was introduced by adding milled NaCl as a porogen. The NaCl crystals were prepared by ball milling (Retsch PM100) the NaCl at 400 rpm for 2 hours (intervals of 5 minutes of milling alternating with 5 minutes of rest). The milling produced NaCl having a particle size of approximately 17-20 μm. The NaCl was added to the solubilized PCL to produce a slurry of polymer and salt at a ratio of 30 vol %/70 vol % polymer/salt. The slurry was mixed in a ball mill for 20 minutes (intervals of 2 minutes of mixing alternating with 2 minutes of rest). Subsequently, the PCL+salt slurry was used for creating films and open tubes.

To produce polymer films, the PCL+salt slurry was cast with an automated tape casting coater (MTI Corporation). Slurry was poured onto copper foil (McMaster) and spread using a blade to produce a film having a final dry thickness of 130-150 μm. The films were air dried and detached from the copper foil by wetting in ethanol. Prior to embossing, the film (PCL+salt) was pressed using an automated calender, in sequential stages, to a final thickness of 80-90 μm.

Open tubes were made by dipping a stainless-steel rod having a 1.6-mm outer diameter (grade 304, McMaster) into the polymer+salt slurry. Once dry, the coated rod was immersed in ethanol and the tube was formed by sliding the PCL+salt tube off the rod.

Embossing materials preparation. Stainless-steel wires (304 stainless steel, annealed; California Fine Wire Company) having an outer diameter of 280 μm were cleaned in ethanol. Clean wires were dipped into a solution of 12 wt % poly(vinyl alcohol) (Sigma Aldrich, 80% hydrolyzed; PVA) in water that was pre-heated to 60° C. Coated wires were hung to dry and then inspected for drips or inhomogeneities in the coating. If drips or inhomogeneities in the coating were found, the wires were excluded from manufacturing. An acetal embossing mold (DELRIN) was machined to have linear grooves separated by 135 μm. Each groove was made with a 0.013-inch endmill, resulting in features that were approximately 300 μm wide and approximately 150 μm deep. A mold for pressing the final multichannel roll together was constructed from aluminum. The mold comprised two pieces registered to produce a single channel of 1.6-mm diameter when fit together.

Embossing. For embossing, two aluminum blocks and the pressing mold were heated to 40-50° C. prior to use. The embossing mold was used at temperatures between approximately 21° C. to 80° C. Sheets of 2-mm foam (Darice) were cut to the size of the embossing mold. Two squares of pressed film (e.g., produced as described above) were cut to size. A first film was laid on the embossing mold and covered by a piece of foam. The sandwich was placed between the pre-heated aluminum blocks and put in a hydraulic press (Carver). The stack was pressed with a force of less than 0.4 metric tons. The block, with film lightly adhering to the surface, was gently removed from the stack. Pre-coated stainless-steel wires were placed in the grooves on the embossing mold and held in place with adhesive tape. In an exemplary embodiment, 16 wires were used to produce a 1.6-mm diameter device. The second film was placed over the top and covered by a piece of foam. The sandwich was placed between the aluminum blocks on the press. The entire stack was pressed with 1.5 metric tons of force for 20 seconds and then removed from the press.

Device manufacture. To form a device, the embossed film with wire spacers was peeled from the embossing block. Excess film on either side of the spacers was cut away with a razor. The device was rolled around an axis parallel to (or substantially parallel to) the axis of the spacers. The roll was placed into a pressing mold pre-heated to 40-50° C. This mold was placed between the two aluminum blocks and pressed to 1.5-2 metric tons of pressure. Once removed from the press, the mold was opened and the roll was removed. The roll was inserted into an open tube and the assembly was immersed into water to remove the porogen (NaCl) and the PVA coating. The assembly was soaked for 1 hour, changing the water at least once. After removal from the water, the spacers were removed with tweezers, and the device was left to air dry.

Nanoparticles. Porous silicon nanoparticles were produced having desired sizes using an electrochemical perforation etch technique as previously described (see, e.g., Qin et al. (2014) "Size Control of Porous Silicon Nanoparticles by Electrochemical Perforation Etching" Part Part Syst Charact. 31: 252-56, incorporated herein by reference). Further, proteins were trapped in the porous nanoparticle matrix using oxidation trapping, which retains protein activity, as previously described (see, e.g., Kim et al. (2016) "Facile Surface Modification of Hydroxylated Silicon Nanostructures Using Heterocyclic Silanes" J Am Chem Soc. 138: 15106-9, incorporated herein by reference). During the development of embodiments of the technology described herein, porous silicon nanoparticles (pSiNPs) having a diameter (e.g., an average diameter) of approximately 200 nm (e.g., 150, 155, 160, 165, 170, 175, 180, 185, 190, 195, 200, 205, 210, 215, 220, 225, 230, 235, 240, 245, or 250 nm)

were prepared using the methods described above. The pSiNPs were stored at a concentration of 1 mg/ml in ethanol, at room temperature, until ready to load with a therapeutic agent (e.g., protein and/or drugs). See also U.S. Pat. No. 7,713,778, incorporated herein by reference, describing methods of generating three-dimensional nanoparticles and depositing materials into nanoparticle pores that find use herein.

Drug/protein loading into nanoparticles. During the development of embodiments of the technology, lysozyme found use as a model protein for experiments to test the delivery of a therapeutic agent according to the technology described herein. In particular, lysozyme was loaded into the pSiNPs in a series of steps. First, a lysozyme stock solution of 10 mg/ml lysozyme (Sigma Aldrich) in tris-buffered saline (TBS) was prepared. Next, pSiNPs were collected from ethanol storage solution by centrifugation (e.g., for 10 minutes at 16,000 rcf) to pellet the pSiNPs and the ethanol supernatant was removed and retained. This first supernatant was placed into new microcentrifuge (e.g., EPPENDORF) tubes and centrifuged again (e.g., for 10 minutes at 16,000 rcf) to collect any nanoparticles present in the first supernatant. The supernatant from the second centrifugation was discarded. The nanoparticles were resuspended in the 10 mg/ml lysozyme stock solution prepared previously (e.g., at 1 mg pSiNP/ml lysozyme stock solution, which corresponds to 10 mg lysozyme/mg pSiNP) by sonification for 5 minutes (Cole Parmer 8891). The lysozyme-particle suspension was gently rocked overnight at 4° C. to load the nanoparticles with lysozyme. After loading, the particles were washed twice. To wash, the loaded particles were pelleted from the solution by centrifugation (e.g., for 10 minutes at 16,000 rcf) and the supernatant was removed and deionized (DI) water was added. The pellet of loaded nanoparticles was then sonified for 5 minutes at room temperature. If it was necessary to concentrate particles prior to incorporating them into a polymer device (e.g., a scaffold), concentration of particles was performed using DI water and consecutive washes. The pellet was used immediately. The same process was used to load nanoparticles with growth factor (BDNF, R&D SYSTEMS, 248BD005) with the following modifications: a stock solution of brain-derived growth factor in PBS was prepared as above and included bovine serum albumin (BSA) at less than 1 wt %. For BDNF loading, washes were used to remove residual BSA from the outside of the nanoparticles using DI water. During the development of embodiments of the technology, experiments indicated that residual BSA on the nanoparticles prevented the formation of a polymer film as described herein.

Incorporation of drug-loaded particles into films/scaffolds. To produce polymer films and/or polymer devices (e.g., scaffolds) comprising loaded nanoparticles, the loaded pSiNP (comprising loaded protein) in DI water were centrifuged into a pellet, the supernatant removed, and the pellet was resuspended in ethanol by sonification. The amount of ethanol added approximately between 100-300 µl to maximize the concentration of nanoparticles in the ethanol suspension. This concentrated mixture was transferred to a glass vial for preparing a slurry comprising polymer and porogen (e.g., salt). A polymer slurry was prepared from 4.5 wt % poly(lactide co-glycolide) (85:15, molecular weight 65-95 kDa, Expansorb 10P008; PLGA) in chloroform. The porogen (NaCl) and polymer slurry was prepared and mixed as described above to produce a slurry having 70 vol % porosity.

The PLGA+salt slurry was added to the loaded nanoparticles to provide a PLGA+salt+nanoparticle slurry used to produce a film comprising nanoparticles at 5, 10, or 15 wt % of the solid portion of the final film. The slurry and nanoparticles were homogenized by sonification at room temperature for 3-5 minutes until the slurry had a homogenous brown color from distribution of the nanoparticles throughout the slurry. The slurry was then cast into a film on a glass sheet using an automated tape caster as described above. The film was air dried, wetted in ethanol, and removed from the glass using a razor blade. The films comprising pSiNPs were stored at 4° C. until use.

The embossing method described herein was used to create a multichannel device providing spatial and/or temporal control of therapeutic agent release. For instance, to produce a device comprising two different concentrations of nanoparticles and/or therapeutic agent, two films were prepared as described herein comprising two different concentrations of nanoparticles and/or therapeutic agent and the two pieces of film were placed on the embossing block with a 1-mm overlap. This placement determined the spatial distribution of release in the device. Temporal distribution and release of therapeutic agent was a property of the polymer, film, and its release kinetics. At least one of the films was porous PLGA+pSiNP as described above. In areas of the device where no drug release was desired, a porous PCL film was used (prepared as described above) that did not comprise drug-loaded pSiNPs. The steps of the embossing process were followed as described above with no other changes, including the use of pre-coated stainless-steel wires (e.g., to provide channels) and a top layer of porous PCL film. Assembly of the embossed films into a multichannel device and insertion of the device into an outer conduit was also the same as described above.

Materials characterization assays. Unless explicitly stated, materials characterization was performed on films after removing the porogen from the materials.

White light interferometry was used to measure the surface roughness of films. Roughness measurements were obtained using a white light interferometer (Zygo New View 5000) with and without 15 wt % pSiNPs. Dry samples were cut to 1 cm$^2$. Roughness was reported as the root mean squared roughness (Rq) of the films over a 640×640 µm$^2$ area. Surface roughness images were collected over an area of 640×640 µm$^2$.

The tensile strength of PLGA films with and without 15 wt % pSiNP were tested. Rectangular samples were cut from the films to be 8 mm×30 mm and the samples were hydrated overnight in phosphate buffered saline (PBS) at 37° C. prior to testing. Tension tests were performed at room temperature at a rate of 1 mm/min until material failure (TA XT plus texture analyzer). The elastic modulus was calculated as the linear portion of the stress-strain curve.

Materials were assessed by scanning Electron Microscopy (SEM). Dry samples were sectioned with a razor blade before placing them on an aluminum stub for microscopy. For secondary electron images (topography only), all samples were sputter coated with gold for 4 minutes at 40 mA and imaged using a Hitachi S-3500N operating at 20 keV and at a working distance of 10 mm. For backscattered electron images, a dot of silver paste (PELCO@Colloidal Silver Paste) was placed on a corner of the films and they were imaged without further coating using a MIRA3 Tescan operating at 15 keV and at a working distance of 15 mm.

Experimental details for data reported. Lysozyme release was measured using lysozyme-loaded pSiNPs incorporated into films at various wt %. Film samples were washed out for 30 minutes in tap water and dried at room temperature. Film samples were weighed and then placed into Eppendorf tubes. The release experiment was carried out in PBS at 37° C. PBS was removed from the film sample every 3 to 4 days and replaced with fresh PBS. The supernatant was then used to calculate the release of active protein (lysozyme activity kit, Sigma Aldrich, LY0100) and the total protein released (Thermo Scientific Pierce Micro BCA Protein Assay Kit, ThermoFisher Scientific). Lysozyme activity was determined on the day of harvest. Total protein calculations were run on samples that were left at room temperature for at least 14 days to allow any residual nanoparticles to degrade. Release was reported per mg of scaffold. Two types of control films were prepared. A first control film was prepared with pSiNPs that had not been loaded with lysozyme. A second control film was prepared by adding lyophilized lysozyme directly to the polymer+salt slurry, without incorporation into pSiNPs, and sonifying the slurry as before.

BDNF release from pSiNPs was examined as for lysozyme with the following modifications. The protein was released into PBS containing 0.1% BSA and the supernatant was harvested every 2 days. The BDNF concentration was quantified immediately upon harvest using an ELISA kit.

Neurite outgrowth was assayed using porous film inserts. Washed films were cut into pieces of 12×8 mm and sterilized by immersing in 100% ethanol for 5 minutes, followed by two washes with sterile water. Films were assembled into 24-well inserts in a sterile biological cabinet (CELL-CROWN, Z681903-12EA). Each sample comprised two layers: 1) a bottom layer of non-porous PCL cut to a circle of 24 mm diameter; and 2) a top layer of porous film. After assembly, the inserts were placed at the bottom of a 24-well tissue culture plate and 400 µl of sterile water was added. Inserts were stored at room temperature in a sterile hood for two days until use. Several hours prior to seeding the neurites, films were coated with laminin (natural mouse laminin, Invitrogen, 23017-015). Each insert was incubated with 4 µg laminin in PBS for 1 hour at room temperature and then washed with PBS. Inserts were left in PBS at 37° C. until seeding. Dorsal root ganglion (DRGs) were explanted from adult mice, cut into four pieces each, and left in PBS until seeding. Explant pieces were placed on inserts (one per insert) by pipetting 5 µl of PBS+explant onto the film surface. The explants were incubated for 2 hours at 37° C. to attach the explants to the films before adding 400 µl of complete cell culture media to the well. Media was exchanged every 3-4 days. After 7 days of culture, the explants were fixed in 4% paraformaldehyde for 15 minutes. The samples were then fluorescently labeled to detect β-tubulin (1:1500, TUJ1, Promega, G7121). Briefly, films were washed in PBS+0.1% Tween-20 (PBST), then blocked with 5 wt % BSA in PBST for 1 hour at room temperature. After washing twice in PBST, samples were incubated with primary antibody in 3 wt % BSA in PBST overnight at 4° C. Following two PBST washes, secondary antibody (1:1000, AlexaFluor) diluted in PBS was incubated with the samples for 1-2 hours at room temperature. Finally, samples were washed twice with PBS and left in a solution of PBS and DAPI stain (NucBlue Fixed Cell ReadyProbes Reagent, ThermoFisher Scientific, R37606), 2 drops per ml PBS). Inserts with explants were imaged using a Cytation 5 imaging reader (BioTek). Neurite outgrowth was calculated using an Image J plugin called Neurite-J 1.1 (see, e.g., Torres-Espin et al. (2014) "Neurite-J: An Image-J plug-in for axonal growth analysis in organotypic cultures" J Neurosci Methods. 236: 26-39, incorporated herein by reference). Neurite outgrowth is reported as the maximum length reached by the neurites (perpendicular to the explant body), normalized by the distance cells migrated (calculated from the average distance away from the explant body where cell nuclei were found seen).

Example 1—Embossed Sheet with Linear Features and Intrinsic Porosity

During the development of embodiments of the technology provided herein, experiments were conducted to produce (see, e.g., Materials and Methods), test, and/or characterize an embossed sheet with linear features and intrinsic porosity. Polymer film sheets were made by film casting a composition comprising polycaprolactone (PCL) and NaCl as a porogen. In an exemplary embodiment, films comprised 70 vol % of a NaCl porogen that had been previously milled to a diameter of less than 20 µm. Polymer film sheets were embossed on an embossing block (see, e.g., FIG. 1) at 21° C., 40° C., and 60° C. After embossing the polymer film sheets, the NaCl porogen was removed from the film by washing the film in water.

Figure 2:
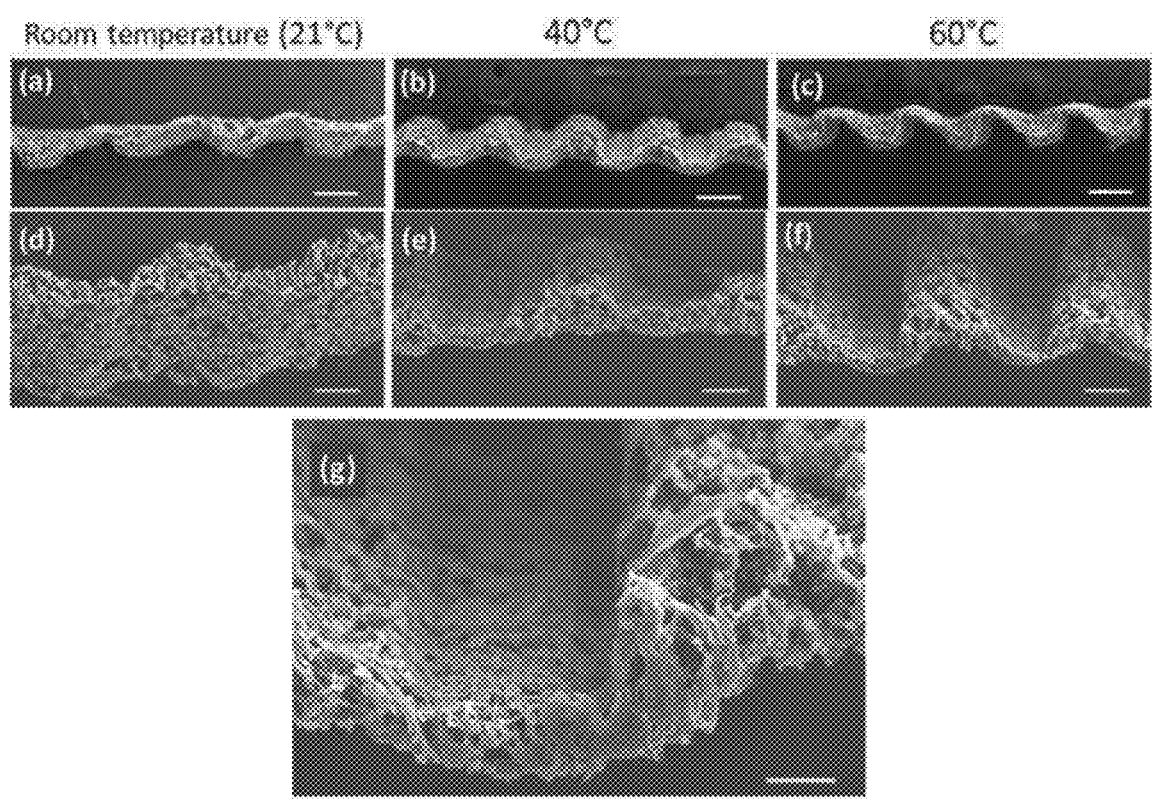
FIG. 2 is a series of micrographs showing cross-sections of PCL films embossed at different temperatures (21° C., 40° C., and 60° C.). Panels (a)-(c) show the films as embossed; panels (d)-(f) show the embossed films after washing away the salt porogen; and panel (g) shows an embossed film after washing away the porogen at a higher magnification to show the porosity of the embossed film. Scale bar in panels (a)-(c) shows a distance of 300 µm; scale bar in panels (d)-(f) shows a distance of 150 µm; scale bar in panel (g) shows a distance of 50 µm.

Measurements of the films indicated that the films had linear features and an intrinsic porosity that remained after removal of the porogen. In particular, micrographs of embossed films indicated that films comprised linear features produced by embossing on the embossing block and pores produced by the porogen (see, e.g., FIG. 2, panels (a) to (g)). Further, the micrographs indicated that the film thickness decreased with increased embossing temperature (see, e.g., FIG. 2, panels (a) to (c) and (d) to (f)) and that the embossed features more closely reproduced the geometry of the embossing mold with increased temperature (see, e.g., FIG. 2, panels (a) to (c) and (d) to (f)). The micrographs indicated that the films comprised pores after washing out the porogen (see, e.g., FIG. 2, panels (d) to (g)).

Example 2—Embossing with Incorporation of a Spacer Material

During the development of embodiments of the technology provided herein, experiments were conducted to produce (see, e.g., Materials and Methods), test, and/or characterize a porous material comprising void spaces (e.g., linear void spaces). Two sheets of polymer film and a series of spacer wires (placed between the polymer film sheets) were embossed on the embossing block (see, e.g., Materials and Methods). In an exemplary embodiment, the wires were stainless steel and coated with polyvinyl alcohol. After applying pressure, the spacer wires were removed.

Figure 3:
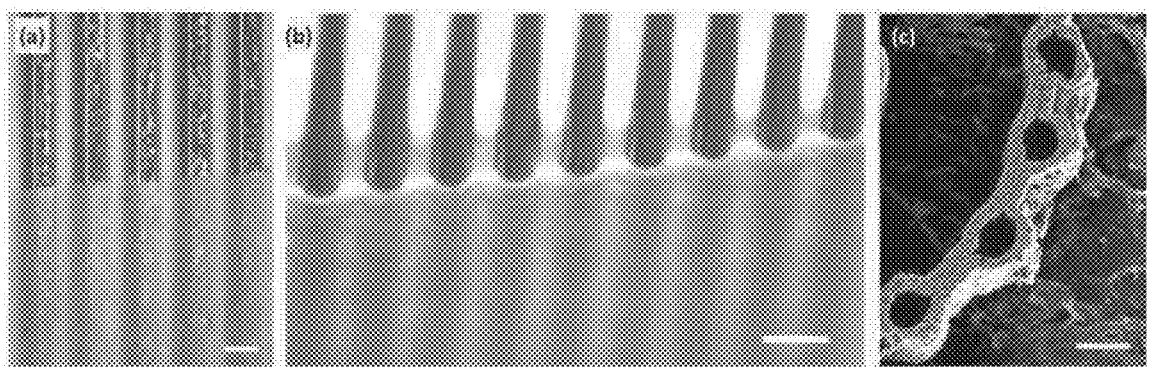
FIG. 3 is a series of micrographs showing a series of spacers in an embossed sheet. Panel (a) shows a side view and panel (b) shows a top view. Panel (c) shows the embossed film after removing the spacer to produce void spaces. Scale bar in panel (a) shows a distance of 250 µm; scale bar in panel (b) shows a distance of 500 µm; scale bar in panel (c) shows a distance of 300 µm.

Examination of the polymer films embossed using the spacer wires indicated that placing the spacer (e.g., wire mandrel coated with poly vinyl alcohol (PVA)) into the features creates filled design and that the spacer can be removed to make a void space. FIG. 3, panel (a) shows the wire spacer in an embossed sheet from a side view and FIG. 3, panel (b) shows the wire spacer in an embossed sheet from a top view. FIG. 3, panel (c) shows the embossed material comprising void spaces after removing the spacer wires.

Example 3—Embossed Devices

During the development of embodiments of the technology provided herein, experiments were conducted to produce (see, e.g., Materials and Methods; see also FIG. 5, panel (a)), test, and/or characterize a device comprising a porous polymer material and microscale features (see, e.g., FIG. 5, panels (a)-(c)). Polymer films were produced and a material comprising void spaces was produced (see, e.g., Materials and Methods and Example 2). The material was rolled and inserted into a tube to produce an embossed device (see, e.g., FIG. 4, panel (b) and FIG. 5, panel (c)).

Figure 4:
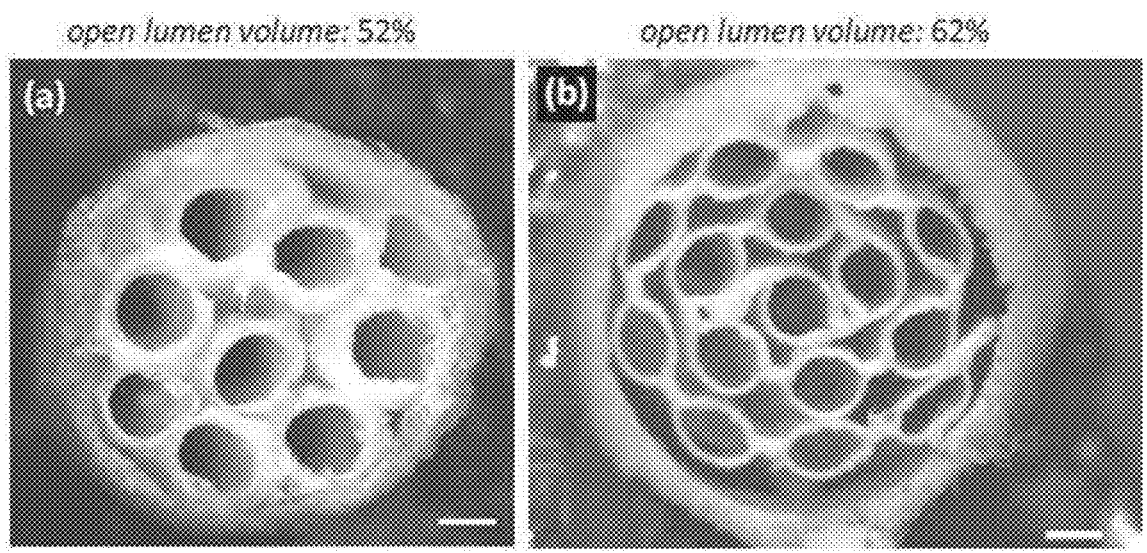
FIG. 4 is a series of micrographs showing devices produced from porous PCL to comprise linear microchannels. The device shown in panel (a) was produced by conventional dip coating methods and the device shown in panel (b) was produced by an embodiment of the embossing methods described herein. The device shown in panel (a) produced according to previous dip coating methods had an open lumen volume of 52 vol % and the device shown in panel (b) produced according to the technology described had an open lumen volume of 62 vol %. The scale bar indicates a distance of 250 µm.

Examination of the embossed device (FIG. 4, panel (b)) indicated that it closely resembled microchannel devices manufactured using dip-coating coating methods (see, e.g., FIG. 4, panel (a)). However, devices produced according to the embossing technology provided herein are improved in several ways relative to devices produced by dip coating. First, materials and devices produced according to the technology described herein can comprise a greater range of materials and material types than can be used in dip coating methods. Second, materials and devices produced according to the technology described herein can be functionalized and/or modified in more ways than materials and devices produced by dip coating methods. Finally, materials and devices produced according to the technology described herein have an increased lumen volume relative to materials and devices produced by dip coating. In particular, materials and devices produced by dip-coating techniques have been measured to have open lumen volumes of approximately 50 vol % or less (e.g., an open lumen volume of approximately 45 vol % to 52 vol %) (see, e.g., FIG. 4, panel (a) and Table 1).

TABLE 1

Characterization of multichannel scaffolds produced by present methods

| Material | Channel diameter (µm) | Wall Thickness (µm) | Open lumen volume (%) |
| --- | --- | --- | --- |
| non-porous PCL | 200 | 61.5 ± 2.7 | 62.4 ± 0.6 |
| porous PLGA | 200 | 95.1 ± 7.5 | 50.7 ± 3.3 |
| porous PCL | 200 | 94.8 ± 5.5 | 47.9 ± 2.7 |
| porous PLGA | 300 | 111.2 ± 9.3 | 47.2 ± 2.7 |
| porous PCL | 300 | 87.1 ± 4.7 | 52.3 ± 0.3 |

In Table 1, non-porous scaffolds were produced by extrusion methods. Porous scaffolds were produced by dip coating methods.

In contrast, embossed materials and devices produced according to the technology described herein have open lumen volumes that are greater than 60 vol % see FIG. 4, panel (b)). Measurements of embossed devices indicated that the embossed materials have a decreased wall thickness than dip coated materials. In addition, embossed devices have more uniform features than dip coated devices. Both dip-coated and embossed devices have comparable mechanical properties and flexibility.

Figure 6:
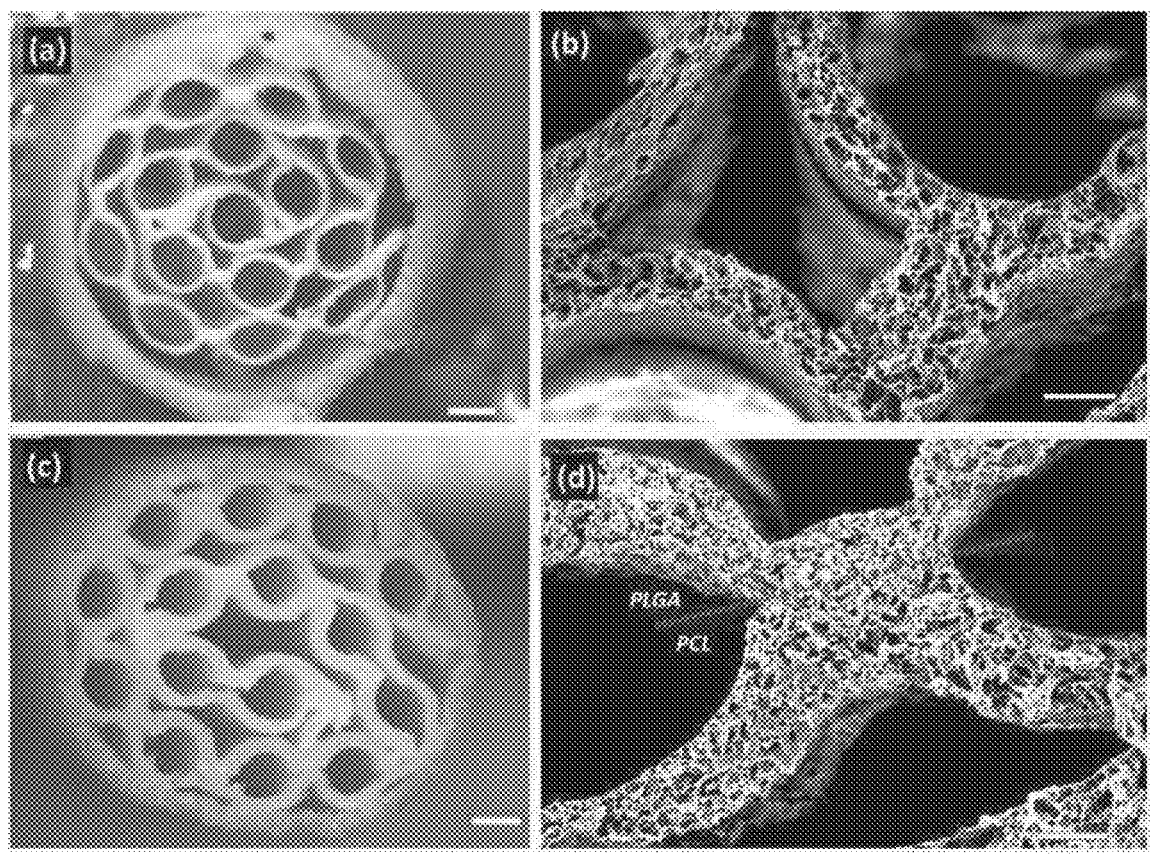
FIG. 6 is a series of micrographs showing embodiments of devices produced according to the technology described herein. The devices comprise 300-µm linear features and have a 70 vol % porosity. The devices shown in panels (a)-(b) were produced from polycaprolactone (PCL) and the devices shown in panels (c)-(d) were produced from a combination of PCL and poly(lactide-co-glycolide) (PLGA). The micrographs shown in panels (a) and (c) show the macroscopic cross-sections of devices. The micrographs shown in panels (b) and (d) show the intrinsic porosity and close, physical bond between film layers. The scale bar in panels (a) and (c) indicates a distance of 250 µm. The scale bar in panels (b) and (d) indicates a distance of 50 µm.

Experiments were conducted during the development of embodiments of the technology described herein to produce, test, and/or characterize embossed devices made from different polymers. In particular, embossed devices were made from polycaprolactone (PCL) (FIG. 6, panels (a) and (b)) and a combination of PCL and poly(lactide-co-glycolide) (PLGA) (FIG. 6, panel (c) and (d)). These devices comprised 300-µm linear features and were produced to have 70 vol % porosity. FIG. 6 shows the macroscopic cross-sections of the PCL (FIG. 6, panel (a)) and PCL/PLGA (FIG. 6, panel (c)) devices. Micrographs show the intrinsic porosity and close, physical bond between film layers for the PCL (FIG. 6, panel (b)) and PCL/PLGA (FIG. 6, panel (d)) devices.

Figure 7A:
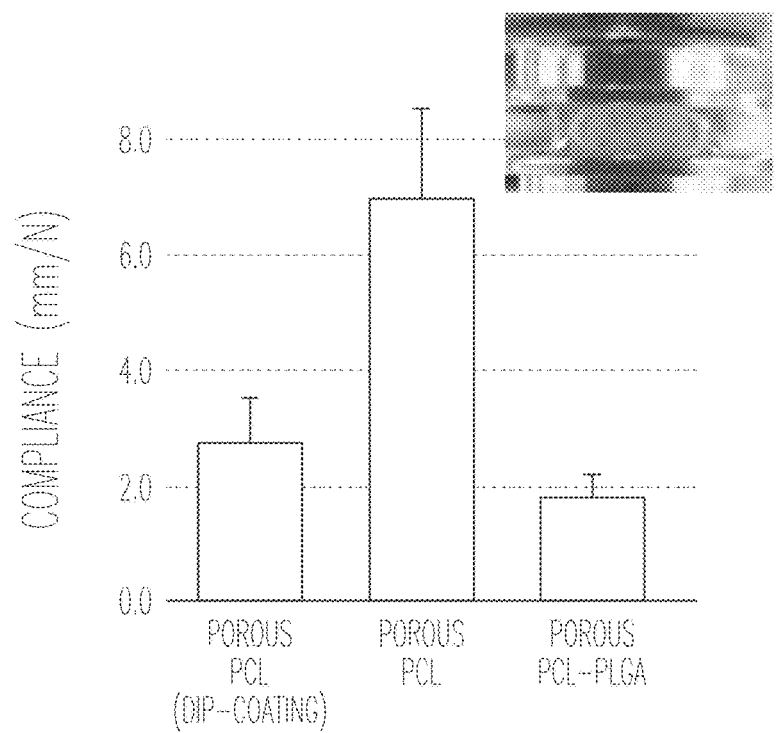
FIGS. 7A and 7B show bars plots of measurements characterizing the mechanical properties of hydrated devices produced by dip coating methods (left bars in FIGS. 7A and 7B and according to embodiments of the technology described herein (middle and right bars in FIGS. 7A and 7B.
Figure 7B:
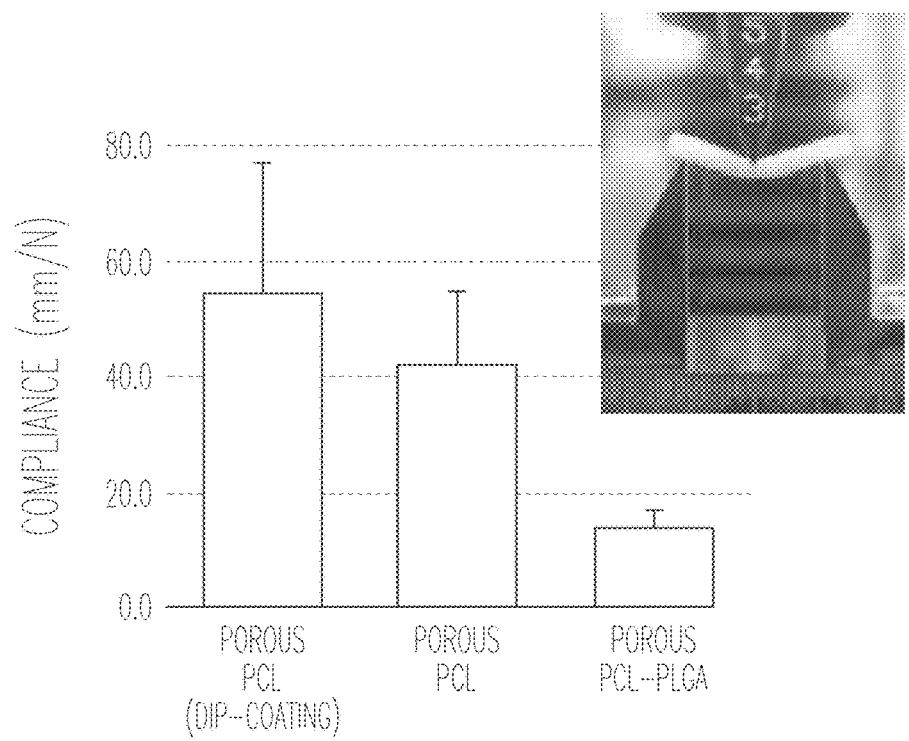

Experiments were conducted during the development of embodiments of the technology provided herein to characterize the mechanical properties of embossed devices. In particular, data were collected from hydrated embossed devices in tests to measure responses to compression and 3-point bending. Embodiments of the embossing technology described herein were used to produce PCL and PCL/PLGA devices 1.5 mm in diameter and 15 mm long (cross sections shown in FIG. 6, panel (a) (PCL) and (c) (PCL/PLGA). Similar devices were produced from PCL by dip coating for comparison. The data indicated that the hydrated embossed devices were easily compressed (FIG. 7, panel (a)) and bent (FIG. 7, panel (b)). The microchannel devices made by the embossing methods described herein were measured to have equal or greater compliance than dip-coated devices (FIG. 7, panel (a) and (b)). In addition, a large range of properties was observed depending on the material used. Accordingly, embodiments of the technology provide for producing materials having a specified and/or desirable physical characteristic by selecting an appropriate material for forming the embossed device.

Example 4A—Embossed Devices for Nerve Repair

In some embodiments, embossed devices are produced from porous PCL and comprise linear microchannels. The entire device has an inner diameter of 1.6 mm, has a length of 10 mm, and has a 1-mm overhang of the outer sheath on either side (e.g., for suturing in place in a subject). To assess the efficacy of these devices for nerve repair, devices are tested in the rat sciatic nerve model. Animals are housed (e.g., 2-3 per cage) with free access to food and water in facilities approved by the American Association for the Accreditation of Laboratory Animal Care. All animal studies are carried out according to NIH guidelines for laboratory animal care and safety, adhering to protocols approved by the Institutional Animal Care and Use Committee of the VA Healthcare System, San Diego.

To implant embossed devices (n=6), animals are deeply anesthetized (e.g., using ketamine (25 mg/mL), xylazine (1300 mg/mL), and acepromazine (0.25 mg/mL)) before making a 20-mm long incision on the right lateral thigh. The right sciatic nerve trunk is exposed via a lateral gluteal muscle dissection. Epineural connective tissue around the nerve trunk is separated with microscissors and a 6.0-mm long nerve segment is excised. After tissue retraction, the severed nerve stumps are further separated to about 15 mm; they are protected and hydrated with physiological saline. Devices are positioned and attached to the nerve, at either end, using 9-0 Ethicon suture. Devices are positioned to avoid tension at the interfaces of the device and nerve site. Following implantation, muscles are sutured using 5-0 suture and the skin is closed using clips. Antibiotics and analgesics (e.g., banamine (1 mg/kg) and ampicillin (0.2 mg/kg) in Ringer's lactate) are administered for the first 3 days to facilitate recovery from surgery. After 4 weeks, devices are harvested. Animals are perfused with 4% paraformaldehyde (PFA) and the tissue is removed and post-fixed in PFA for another 24 hours followed by 48 hours in 30% sucrose.

After 4 weeks, observations are expected to indicate no sign of degradation of the device. To assess the regeneration of nerves across the lesion site, immunolabeling is performed on histological sections. The tissue is processed for: 1) axon labeling, e.g., to assess axon regeneration through and beyond the injury site (NF200); and 2) Schwann cells (S100).

The microchannels of the embossed device produce an aligned growth of neurites through the length of the scaffold, with nerves exiting the distal side of the implant. Unlike more traditional manufacturing methods (e.g., dip-coating), the high open lumen volume provided by this technique (>50%) allows a greater number of neurons to regenerate due to the reduction of volume taken up by the pore walls. Accordingly, the technology provides for the faster healing of nerve lesions with better functional recovery.

Example 4B—Embossed Devices for Nerve Repair

Figure 16A:
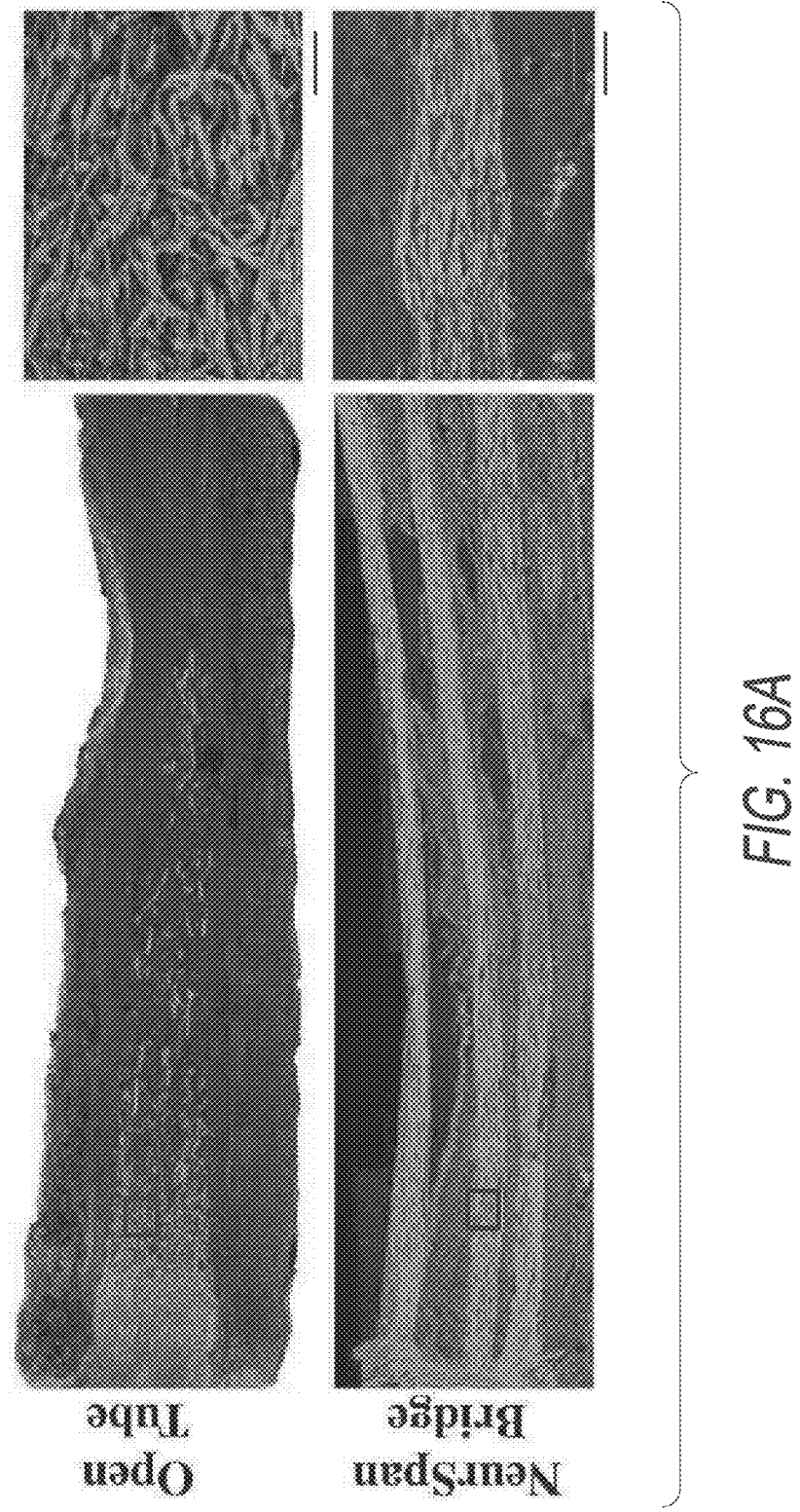
FIGS. 16A-16C is in vivo results from embossed multi-channel scaffolds, (Neurospan Bridge) according to the disclosure, implanted in a 1 cm-long defect in rat sciatic nerve and compared to sural nerve autograft or open tube implant.
Figure 16B:
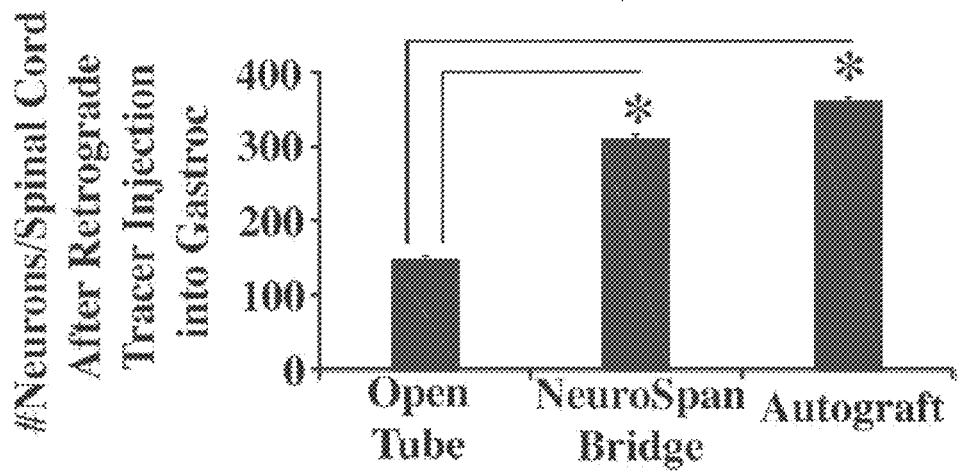
Figure 16C:
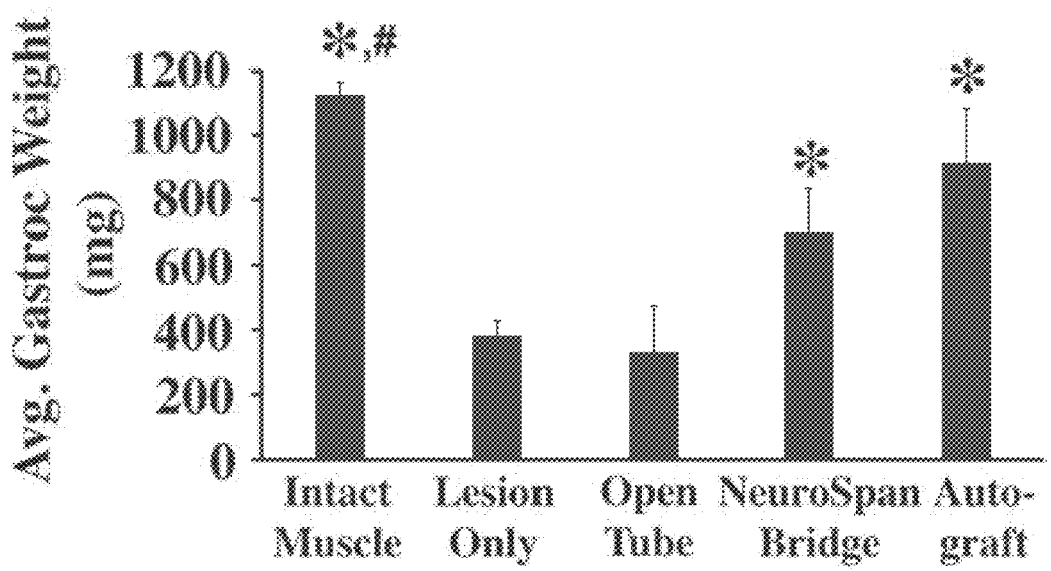

Embossed multichannel scaffolds were implanted in a 1 cm-long defect in rat sciatic nerve and compared to sural nerve autograft or open tube implant. Four weeks post-implant multichannel scaffolds support linear alignment and accelerated regeneration of axons across the injury site. Six months post implant multichannel scaffolds showed improved connectivity between spinal cord and gastrocnemius muscle, compared to open tube treatment and comparable to the autograft. In addition, multichannel scaffolds support increased muscle mass, double the amount of increased muscle mass compared to lesion-only or open tube treatments, and comparable to autograft. See FIG. 16, where the embossed multichannel scaffold is referenced as "NeuroSpan Bridge." FIG. 16 shows (A) superior axonal alignment and faster rate of regeneration across a 1 cm sciatic nerve gap in the rat (shown is four weeks post-injury); (B) improved connectivity between spinal cord motor neurons and muscle, assessed by injection of retrograde tracer (Cholera Toxin B) into gastrocnemius muscle six months after nerve repair; and (C) significantly improved muscle mass. Statistically, the NeuroSpan Bridge is as effective as a sural nerve autograft. N=11 animals per group.

Example 5—Scaling-Up Embossed Devices

Figure 8:
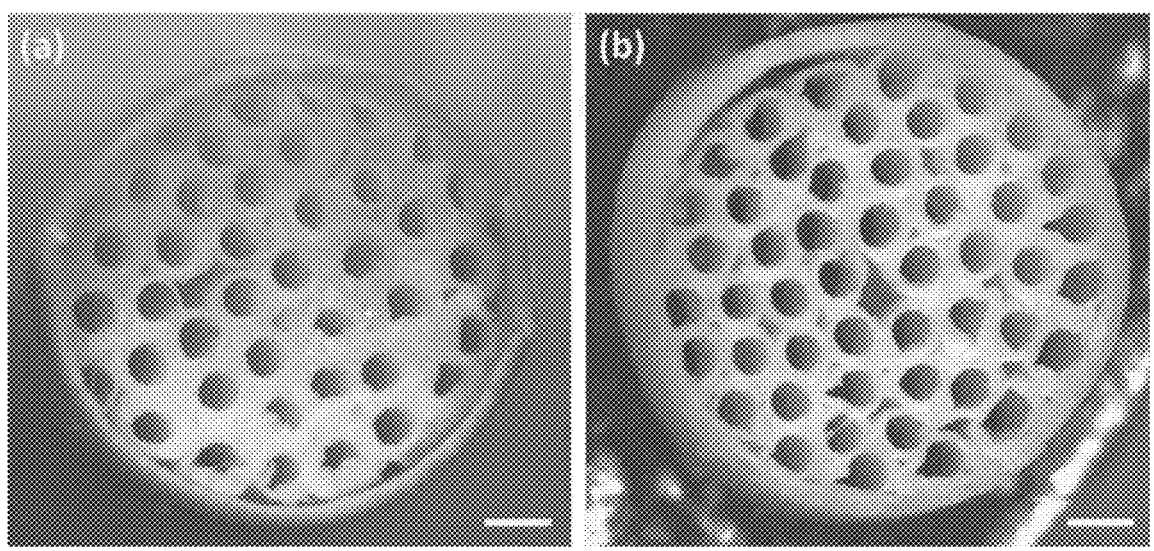
FIG. 8 is a series of micrographs of scaled-up devices. Panel (b) shows an embossed device that retains microscale features. Panel (a) shows a device produced by a traditional manufacturing method (dip-coating). The scale bars in panels (a) and (b) indicate a distance of 500 µm.

During the development of embodiments of the technology provided herein, experiments were conducted to scale-up the methods and compositions described in the examples above to produce a larger embossed device. In particular, a device having a 3-mm diameter was produced using the same methods described in the Materials and Methods, in Example 3, and in FIG. 5, panel (a). Data were collected from testing these larger embossed devices (FIG. 8, panel (b)) and similar, large devices produced by traditional methods (e.g., dip coating) (FIG. 8, panel (a)). These data indicated that the technology is easily scaled up to different aspect ratios and that production time is significantly reduced relative to traditional methods (e.g., dip-coating) with no change in feature size.

Example 6—Tailoring Release Rate of Therapeutic Agent

Figure 9A:
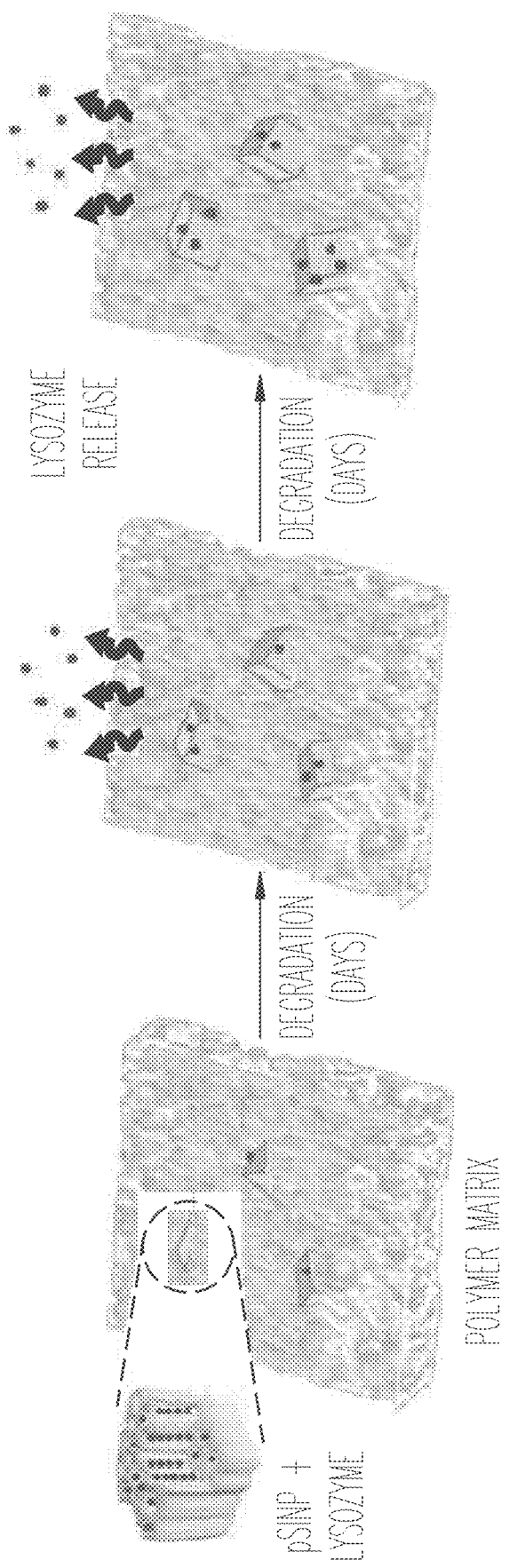
FIG. 9A is a schematic drawing showing the polymer film comprising lysozyme-loaded pSiNPs and release of the lysozyme from the polymer film and pSiNPs as the polymer film degrades under physiological conditions over the course of days.

During the development of embodiments of the technology described herein experiments were conducted to test the release rate of a therapeutic agent using lysozyme loaded-pSiNPs embedded into a polymer sheet. A delivery vehicle comprising a polymer sheet was produced by film casting a slurry of poly(lactide co-glycolide) (PLGA) comprising a porogen (NaCl milled to <20 μm diameter). Polymer sheets comprising pSiNPs were produced by sonifying the lysozyme-loaded pSiNPs in the polymer/porogen slurry prior to casting. Porogen was removed from the films by washing in water. pSiNPs were loaded with lysozyme (prior to incorporation into slurry) as a model therapeutic agent and were incorporated at 0, 5, 10, and 15 wt % into the polymer films. FIG. 9A is a schematic drawing showing the polymer film comprising lysozyme-loaded pSiNPs and release of the lysozyme from the polymer film and pSiNPs as the polymer film degrades under physiological conditions over the course of days.

Figure 9B:
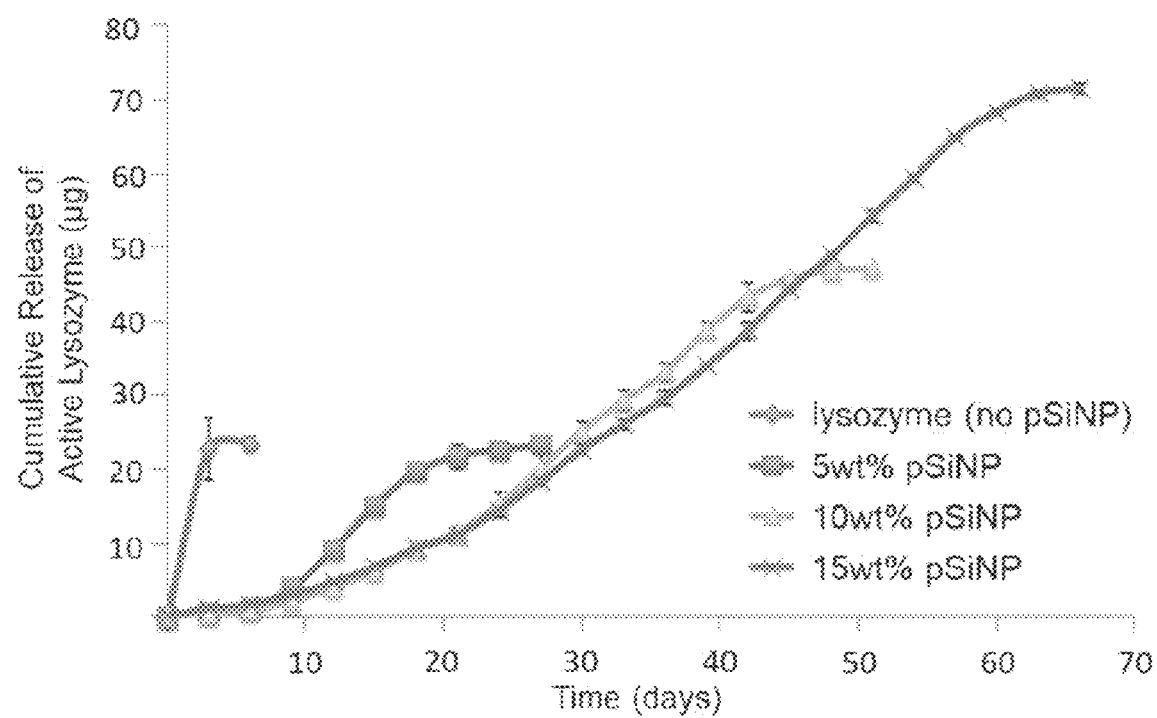
FIG. 9B is a plot of the kinetics of lysozyme release from polymer films comprising pSiNP nanoparticles at 5, 10, and 15 wt %. The data plotted in FIG. 9B indicate that PLGA films comprising lysozyme-loaded pSiNPs released lysozyme over a period of 60 days and that the amount of lysozyme released was dependent on the initial weight percentage of pSiNP in the films. Data plotted as squares were measured for PLGA films comprising lysozyme-loaded pSiNPs at 5 wt %. Data plotted as triangles were measured for PLGA films comprising lysozyme-loaded pSiNPs at 10 wt %. Data plotted as xs were measured for PLGA films comprising lysozyme-loaded pSiNPs at 15 wt %. Data plotted as circles were measured for PLGA films comprising lysozyme only (not loaded into pSiNPs).
Figure 9C:
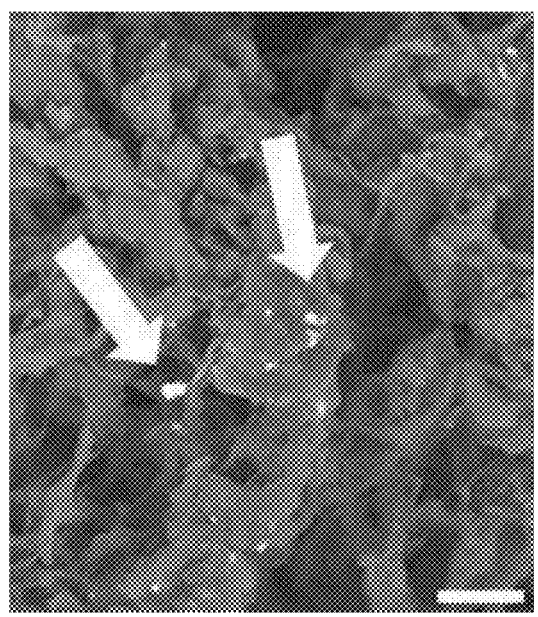
FIG. 9C is a backscattered scanning electron micrograph of a porous PLGA film comprising embedded pSiNPs. The arrows indicate the pSiNPs incorporated into the porous matrix of the polymer film. The scale bar indicates a distance of 10 μm.

The data collected during the experiments indicated that the time and amount of therapeutic agent released from the films was a function of the amount of pSiNP embedded within the polymer (FIG. 9B). Further, data collected during the experiments indicated that the time of drug release was a function of the polymer degradation kinetics. The data plotted in FIG. 9B indicate that PLGA films comprising lysozyme-loaded pSiNPs released lysozyme over a period of 60 days. The amount of lysozyme released was dependent on the initial weight percentage of pSiNP in the films. In particular, the data indicated that PLGA films comprising lysozyme-loaded pSiNPs at 15 wt % actively released lysozyme for more than 50 days (e.g., 51, 52, 53, 54, or 55 days or more). FIG. 9C is a backscattered scanning electron micrograph of porous PLGA films comprising pSiNPs. The arrows indicate pSiNPs in the porous matrix. The scale bar indicates a distance of 10 microns (μm).

Figure 10:
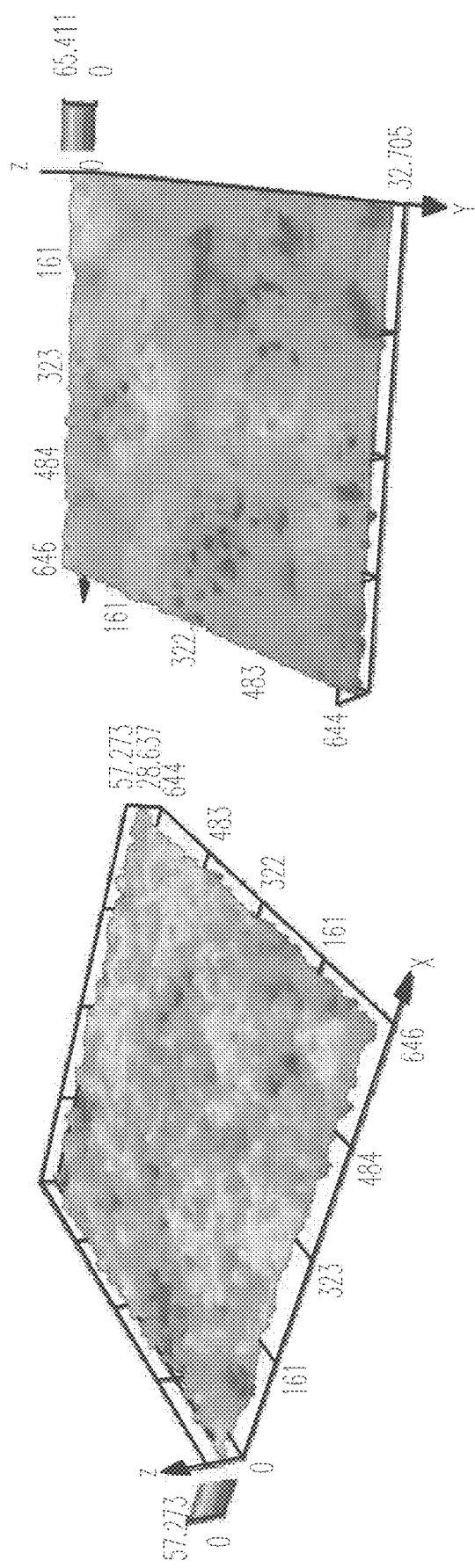
FIG. 10 is a series of plots showing the roughness of polymer films comprising 0 wt % pSiNPs on the left and comprising 15 wt % pSiNPs on the right. Roughness was measured by white light interferometry.

The polymer films were characterized by measuring the elastic modulus of hydrated films in tension and by measuring the surface roughness using white light interferometry (Table 2). The elastic modulus and roughness measurements indicated that embedding nanoparticles into polymer films does not significantly change the film properties. In particular, the elastic moduli and surface roughnesses of PLGA comprising 0 wt % pSiNP and PLGA comprising 15 wt % pSiNP were not significantly different. FIG. 10 shows white light interferometry data collected from 640×640 μm samples of PLGA comprising 0 wt % pSiNP (left image) and PLGA comprising 15 wt % pSiNP (right image).

TABLE 2

Characterization of PLGA films comprising pSiNPs

| Material | Elastic Modulus (MPa) | Roughness (μm$^2$) |
| --- | --- | --- |
| 0 wt % pSiNP | 47.2 ± 8.6 | 3.6 ± 0.02 |
| 15 wt % pSiNP | 35.3 ± 13 | 2.5 ± 0.02 |

Example 7—Delivery of Therapeutic Agents

During the development of embodiments of the technology provided herein, experiments were conducted to test the delivery of a therapeutic agent (e.g., brain-derived neurotrophic factor (BDNF)) from polymer sheets comprising BDNF-loaded pSiNPs. Polymer sheets made by film casting poly(lactide co-glycolide) (PLGA) with porogen (NaCl, milled to <20 μm diameter). Polymer sheets comprising pSiNPs were produced by sonifying BDNF-loaded pSiNPs in the polymer/porogen slurry prior to casting. Porogen was removed from the films by washing in water. pSiNPs were loaded with BDNF (prior to incorporation into slurry) as a model therapeutic agent and were incorporated at 0 and 15 wt % into the polymer films.

Figure 11:
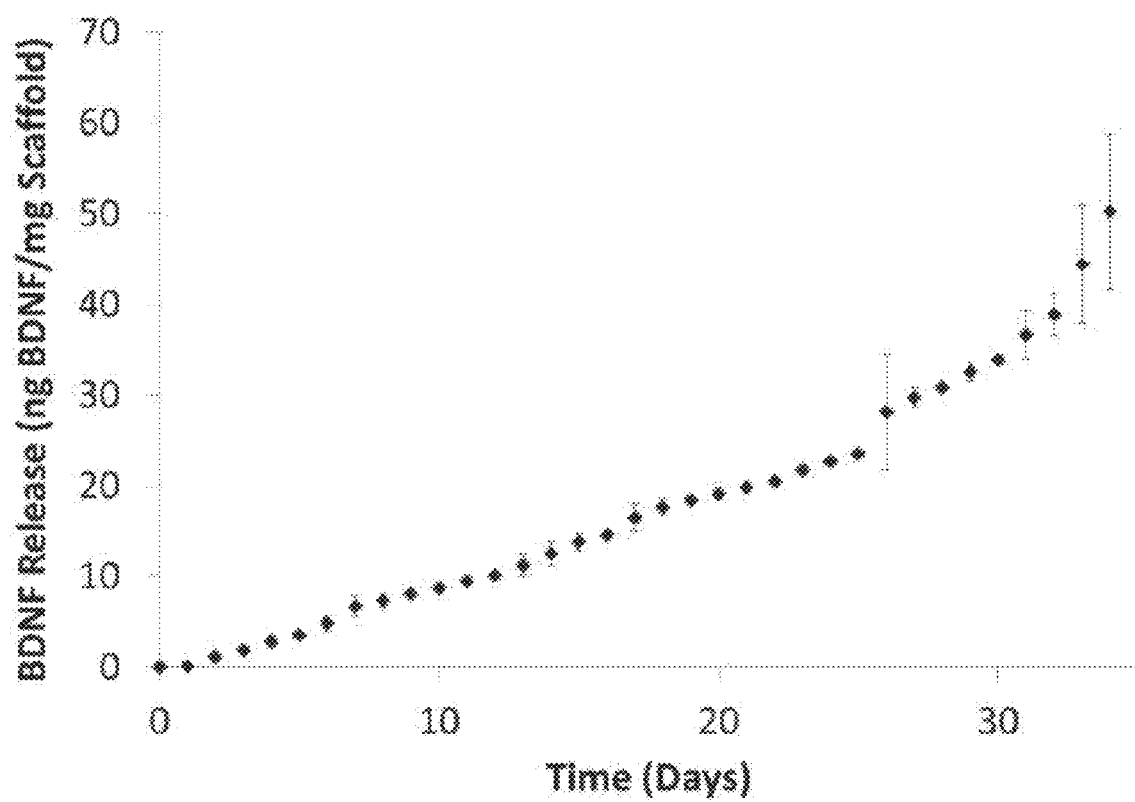
FIG. 11 is a plot of the kinetics of release of a growth factor (BDNF) from a porous polymer (PLGA) film comprising 15 wt % pSiNPs.

FIG. 11 shows the rate of release of BDNF from the polymer films comprising BDNF-loaded pSiNPs at 15 wt %. The data indicated that the polymer films comprising BDNF-loaded pSiNPs delivered 1-2 ng BDNF/mg polymer per day over at least 30 days.

Figure 12A:
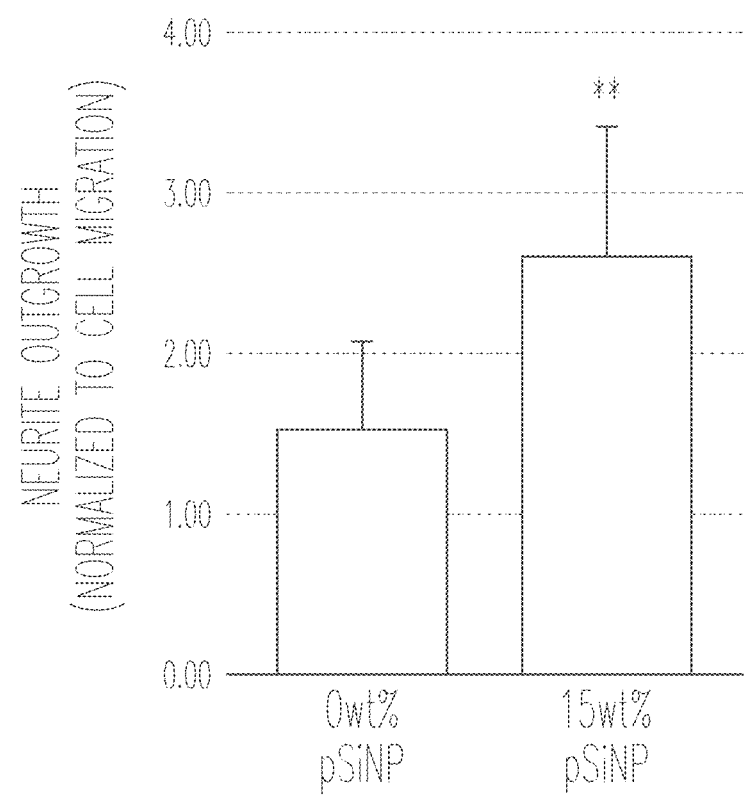
FIG. 12A is a bar plot showing the bioactivity of growth factor (BDNF) released from a PLGA film comprising either 0 or 15 wt % drug-loaded pSiNPs. A significant difference was measured in neurite outgrowth (normalized to cell migration); **$p<0.05$.
Figure 12B:
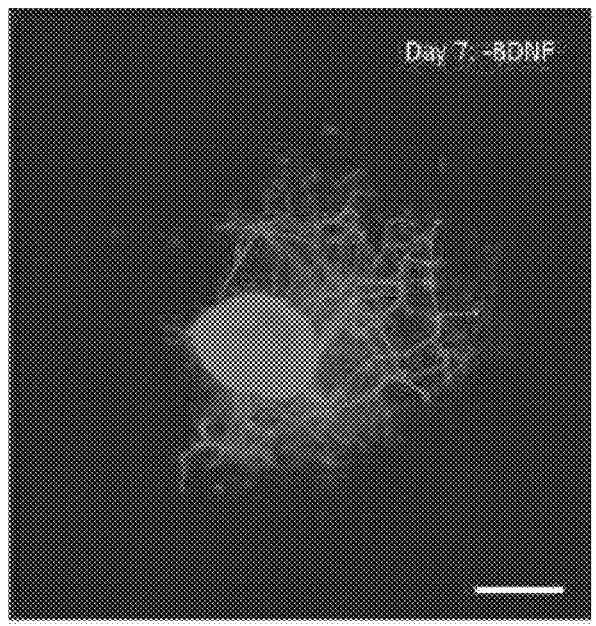
FIG. 12B is a fluorescence micrograph of neurite outgrowth from mouse dorsal root ganglion (DRGs) grown on a polymer film that does not comprise BDNF-loaded pSiNPs. Neurites were visualized using fluorescent staining of TUJ1. The scale bar indicates a distance of 500 μm.
Figure 12C:
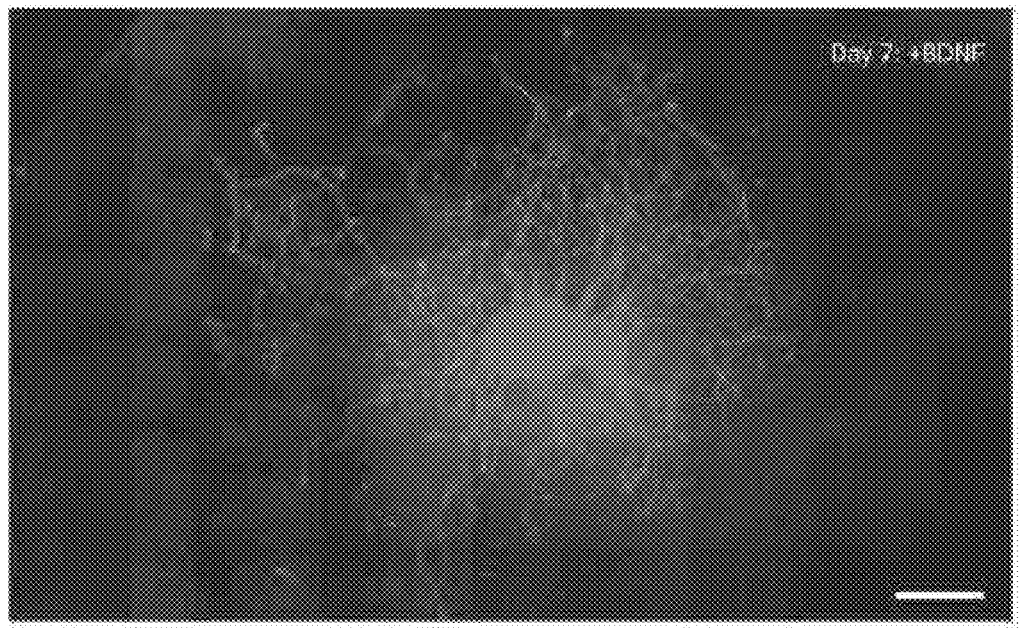
FIG. 12C is a fluorescence micrograph of neurite outgrowth from mouse dorsal root ganglion (DRGs) grown on a polymer film comprising BDNF-loaded pSiNPs at 15 wt %. Neurites were visualized using fluorescent staining of TUJ1. The scale bar indicates a distance of 500 μm.

In addition, the bioactivity of the BDNF was verified and quantified by examining neurite outgrowth on films after 7 days in vitro (FIG. 12). In particular, FIG. 12 shows data describing the bioactivity of growth factor (BDNF) released from a PLGA film comprising either 0 or 15 wt % therapeutic-loaded pSiNPs. First, a significant difference in neurite outgrowth was measured (normalized to cell migration) on the films comprising 15 wt % pSiNPs relative to films comprising 0 wt % pSiNPs (FIG. 12(a)), **p<0.05). Second, neurite outgrowth from mouse dorsal root ganglion (DRGs) was noticeably altered by the addition of BDNF-eluting pSiNPs. FIG. 12(c) shows the increased outgrowth of neurites on polymer films comprising 15 wt % BDNF-loaded pSiNPs relative to FIG. 12(b), which shows limited outgrowth of neurites on polymer films comprising 0 wt % BDNF-loaded pSiNPs. Neurites were visualized in using fluorescent staining of TUJ1. The scale bar in FIGS. 12(b) and 12(c) indicates a distance of 500 microns (μm).

Example 8—Implantable Device for Delivery of Therapeutic Agent

Figure 13A:
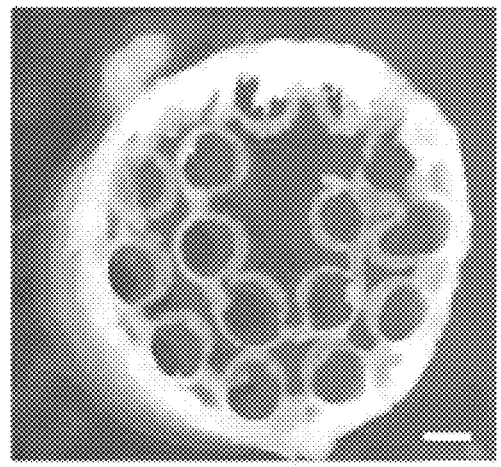
FIG. 13A is an image showing a cross-section of an implantable device produced according to the embossing technology described herein from a polyester film comprising pSiNPs. Addition of the pSiNPs changes the color of the polymer from white to brown (seen in FIG. 13 (panel (a)) as darker grey). The image of the implantable device shows the embossed scaffold with microchannel features. The scale bar indicates a distance of 250 μm.
Figure 13B:
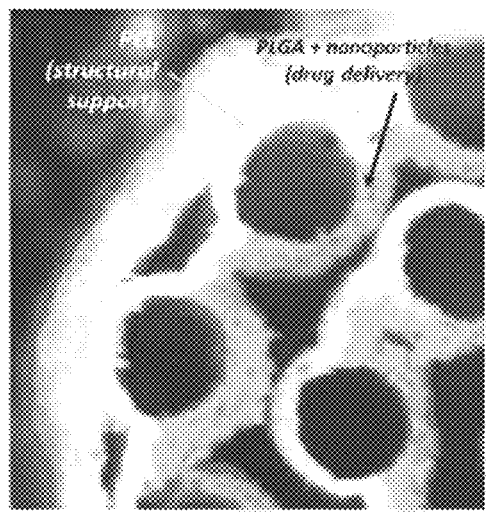
FIG. 13B is an enlarged image showing a cross-section of an implantable device produced according to the embossing technology described herein from a polyester film comprising pSiNPs. Addition of the pSiNPs changes the color of the polymer from white to brown (seen in FIG. 13 panel (b) as darker grey). The enlarged image of the implantable device shows the microchannels and pSiNP incorporation.

During the development of embodiments of the technology, experiments were conducted to prepare and test an implantable device comprising therapeutic agent-loaded pSiNPs (e.g., configured for delivery of a therapeutic agent). The implantable device was prepared using film casting and embossing methods as described herein. Embodiments of the implantable devices were prepared comprising at least two porous polymer films (e.g., comprising PCL, PLGA, and combinations thereof). In some embodiments, devices comprise at least one porous polymer film comprising therapeutic-loaded pSiNPs. In some embodiments, devices comprise a plurality of porous polymer films, wherein each porous polymer film comprises a different therapeutic and/or comprises a different concentration of a therapeutic. Polymer films were produced by embodiments of the embossing methods described herein. In some embodiments, polymer films were produced using a wire spacer (e.g., pre-coated with a release layer, poly(vinyl alcohol) (PVA)) to produce a device comprising channels. After produced the porous polymer films, the films were rolled as described herein to produce a cylinder. In some embodiments, the rolled sheet was inserted into an outer sheath and/or conduit. Removing the porogen and spacers produced a scaffold with a high amount of open lumen volume (FIG. 13(a) and FIG. 13(b)). As shown in FIG. 13(a) and FIG. 13(b), embodiments of the technology provide implantable devices comprising polyester films and pSiNPs. Addition of the pSiNPs changes the color of the polymer from white to brown. Portions of the devices comprising pSiNPs have a darker grey color in FIGS. 13(a) and (b). A cross-section of the embossed device with microchannel features is shown in FIG. 13(a) and an enlarged view of the microchannels shown in FIG. 13(b) indicated the localization of pSiNPs within the scaffold. The scale bar in FIG. 13(a) indicates a distance of 250 microns (μm).

Example 9—Device Providing Spatial and Temporal Control Over Therapeutic Delivery During the development of embodiments of the technology, devices were produced that provide control of the temporal and spatial delivery of a therapeutic. Films were prepared using embodiments of the embossing technology as described herein. The films were used to produce a device having a high open lumen volume and highly engineered control over the time and location of therapeutic release.

In particular, devices were produced that provide control over the temporal release (e.g., release rate, amount released, etc.) of therapeutic from pSiNPs (e.g., from devices comprising pSiNPs). Data collected during these experiments indicated that temporal release is controlled by device characteristics including, but not limited to polymer thickness, polymer degradation kinetics, amount of pSiNPs embedded in the polymer films, size of pSiNPs embedded in the polymer films, and/or pore size and porosity pSiNPs embedded in the polymer films. For example, data collected during these experiments indicated that 15 wt % pSiNP in a porous matrix of 85:15 PLGA had a maximum release of therapeutics between 30 and 40 days post-implantation, while 15 wt % pSiNP in a porous PCL matrix did not begin releasing therapeutics prior to 60 days post-implantation.

Embodiments of the technology provide devices produced by pressing together different films during the embossing process. Embodiments provide that the spatial arrangement and therapeutics are determined and the films produced and arranged accordingly. For example, two or more films are placed on the embossing mold with a 1-mm overlap. After wire spacers and a cover film are placed on top, the assembly is embossed by pressing with 1.5-2 metric tons. This process provides contiguous micro-scale features throughout the device.

Figure 14:
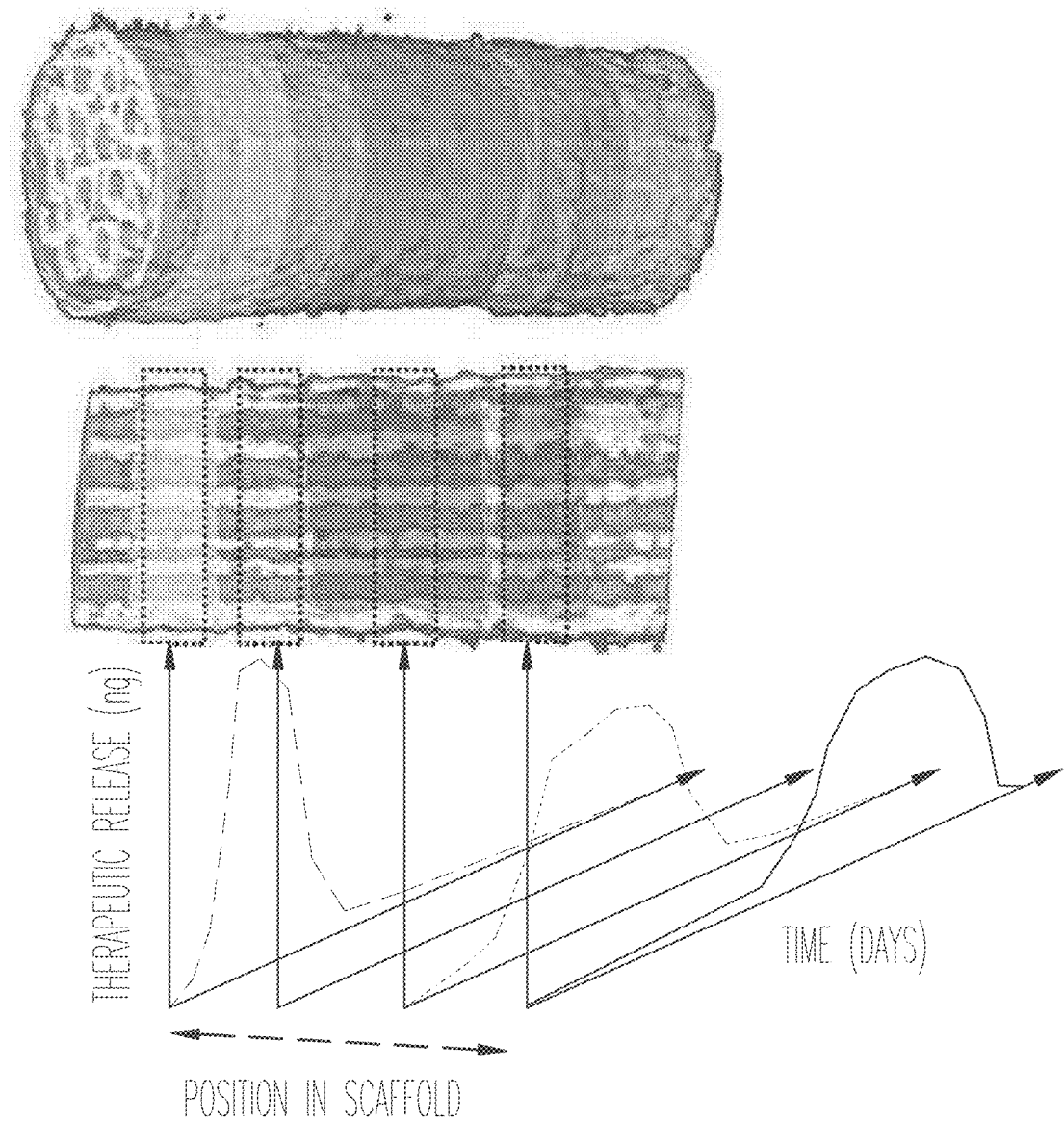
FIG. 14 is a schematic drawing showing a device produced according to an embodiment of the embossing technique described herein. The device provides both temporal and spatial delivery of therapeutics in a single implant. The schematic demonstrates regions within the device comprising different types of therapeutics (denoted in different shades of grey) whose release is controlled by one or more of polymer layer thickness, polymer degradation kinetics, amount of pSiNPs, pSiNP size, pSiNP pore size and porosity, or a combination of any of the foregoing.

FIG. 14 shows a schematic of a device providing both temporal and spatial control of the delivery of a therapeutic. Films comprising different polymers and thus providing different release kinetics (ng released/days) are distributed along the length of the device. Further, the films can comprise different therapeutics and/or different concentrations of therapeutics to provide spatial control of release. Embodiments of the embossing technique thus provide a technology for engineering a device that provides control of both temporal and spatial delivery of therapeutics within a single implant. The schematic in FIG. 14 demonstrates regions within a device comprising different types of therapeutics (denoted in different shades of grey), whose release has been tuned by polymer layer thickness, polymer degradation, amount of pSiNPs, pSiNP size, pSiNP pore size and porosity, or a combination thereof.

Figure 15A:
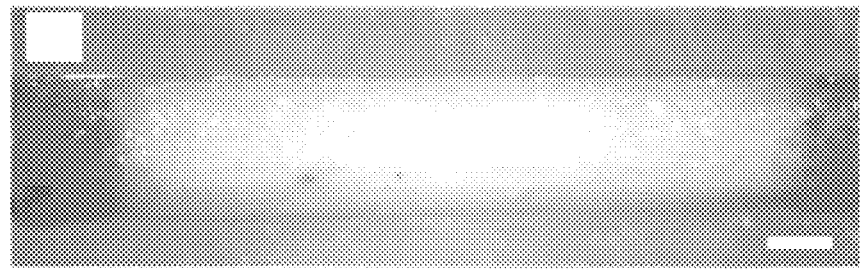
FIG. 15A is an image of a device produced according to an embodiment of the embossing technique described. The embossed implantable device was produced from polyester films comprising pSiNPs. The films were produced to have 300-μm linear features and 70 vol % porosity. The device was designed and produced to comprise separate regions comprising therapeutic-loaded pSiNPs (darker grey color) and not comprising therapeutic-loaded pSiNPs (lighter white color). The image is a macroscopic view of the device demonstrating the three distinct regions of the device: two comprising therapeutic-loaded pSiNPs at the ends and one region not comprising pSiNPs in the middle. The scale bar indicates a distance of 1 mm.
Figure 15B:
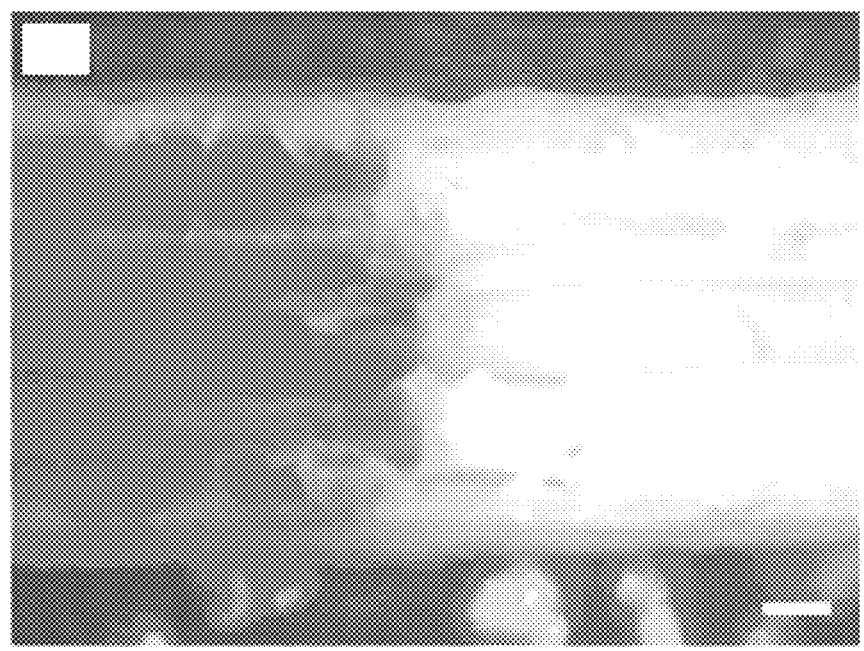
FIG. 15B is an image showing the interface between a region comprising therapeutic-loaded pSiNPs (left, darker grey region) and a region that does not comprise therapeutic-loaded pSiNPs (right, lighter white region) in a device produced according to the technology provided herein. The device comprises coherent features and a physical bond between the two adjacent film layers that form the two regions. The scale bar indicates a distance of 250 μm.

FIG. 15 shows an embodiment of a device providing temporal and/or spatial control of therapeutic delivery. An embossed implantable device was produced from polyesters comprising pSiNPs. The device comprised 300-μm linear features and 70 vol % porosity. The device was engineered so that specific regions of the device comprised therapeutic-loaded pSiNPs (identifiable by the darker grey color in FIGS. 15(a) and (b)). FIG. 15(a) is a macroscopic view of the device demonstrating three distinct regions: two comprising therapeutic-loaded pSiNPs at the ends and one region without pSiNPs in the center. FIG. 15(b) is a photograph showing the interface between the drug-eluting region (left, grey) and non-drug eluting region (right, white). The device comprised coherent features and a physical bond between the film layers. The scale bar indicates a distance of 1 mm in FIG. 15(a) and a distance of 250 microns (μm) in FIG. 15(b).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

What is claimed is:

1. A method for producing a porous film material comprising microscale features and a porosity of 60% vol or more, said method comprising:
   a) providing a polymer film; and
   b) embossing said polymer film to produce said porous film material comprising microscale features; and
   comprising contacting said polymer film with a spacer; and/or
   wherein said embossing comprises pressing said polymer film against a spacer to produce said microscale features in said polymer film.

2. The method of claim 1 wherein said polymer film comprises a porosity of 60% vol or more.

3. The method of claim 1 wherein said embossing comprises pressing said polymer film against an embossing block comprising microscale features.

4. The method of claim 3 wherein said embossing block is heated to 20° C. or more.

5. The method of claim 3 wherein said pressing comprises applying a force of at least 0.1 metric tons.

6. The method of claim 3 wherein said pressing comprises using a hydraulic press.

7. The method of claim 1 wherein providing said polymer film comprises casting a composition comprising a polymer and a porogen.

8. The method of claim 1 wherein providing said polymer film comprises washing a film comprising a polymer and a porogen to minimize and/or eliminate the porogen.

9. The method of claim 1 further comprising washing said porous film material comprising microscale features and a porosity of 60% vol or more.

10. The method of claim 1 wherein said polymer film comprises a biocompatible polymer.

11. The method of claim 1 wherein said polymer film comprises a polyester.

12. The method of claim 1 wherein said polymer film comprises a polycaprolactone and/or a poly(lactide co-glycolide).

13. The method of claim 1 further comprising reacting a surface of said polymer film with a reagent.

* * * * *